(12) United States Patent
    Ward et al.

(10) Patent No.: US 11,312,681 B2
(45) Date of Patent: Apr. 26, 2022

(54) MOLECULAR HOST FRAMEWORKS AND METHODS OF MAKING AND USING SAME

(71) Applicant: New York University, New York, NY (US)

(72) Inventors: Michael David Ward, New York, NY (US); Yuantao Li, Jersey City, NJ (US); Chunhua Tony Hu, Forest Hills, NY (US)

(73) Assignee: New York University, New York, NY (US)

( * ) Notice: Subject to any disclaimer, the term of this patent is extended or adjusted under 35 U.S.C. 154(b) by 36 days.

(21) Appl. No.: 16/435,215

(22) Filed: Jun. 7, 2019

(65) Prior Publication Data

US 2019/0375706 A1    Dec. 12, 2019

Related U.S. Application Data

(60) Provisional application No. 62/681,978, filed on Jun. 7, 2018.

(51) Int. Cl.

| | |
|---|---|
| *C07C 279/02* | (2006.01) |
| *C07C 13/52* | (2006.01) |
| *C07C 309/74* | (2006.01) |
| *C07C 309/73* | (2006.01) |
| *C07C 309/32* | (2006.01) |
| *C07C 309/38* | (2006.01) |
| *C07C 309/35* | (2006.01) |
| *C07C 49/647* | (2006.01) |
| *C07C 49/345* | (2006.01) |
| *C07C 49/603* | (2006.01) |
| *C07C 49/172* | (2006.01) |
| *C07C 211/45* | (2006.01) |
| *C07C 69/587* | (2006.01) |
| *G01N 23/207* | (2018.01) |
| *C07D 307/92* | (2006.01) |
| *C07J 53/00* | (2006.01) |
| *C07J 43/00* | (2006.01) |
| *C07J 7/00* | (2006.01) |

(52) U.S. Cl.
CPC ............ *C07C 309/74* (2013.01); *C07C 13/52* (2013.01); *C07C 49/172* (2013.01); *C07C 49/603* (2013.01); *C07C 49/647* (2013.01); *C07C 69/587* (2013.01); *C07C 211/45* (2013.01); *C07C 309/73* (2013.01); *C07D 307/92* (2013.01); *C07J 7/002* (2013.01); *C07J 43/003* (2013.01); *C07J 53/008* (2013.01); *C07B 2200/13* (2013.01); *C07C 2602/30* (2017.05)

(58) Field of Classification Search
CPC ..... C07C 279/02; C07C 13/52; C07C 309/74; C07C 309/73; C07C 309/32; C07C 309/38; C07C 309/35; C07C 49/647; C07C 49/345; C07C 49/603; C07C 49/172; C07C 211/45; C07C 69/587; G01N 23/207; C07B 2200/13; C07J 53/008; C07J 43/003; C07J 7/002; C07D 307/92

See application file for complete search history.

(56) References Cited

PUBLICATIONS

Custelcean et al., Crystal Growth&Design, vol. 5, No. 6, 2005, 2277-2287.*

* cited by examiner

*Primary Examiner* — Sun Jae Yoo
(74) *Attorney, Agent, or Firm* — Hodgson Russ LLP

(57) ABSTRACT

Crystalline molecular framework:small molecule compounds. The molecular framework is formed from guanidinium cations and organosulfonate anions and the guanidinium cations and organosulfonate anions are associated via one or more hydrogen bond. The small molecule(s) is/are encapsulated by the molecular framework. Methods for making crystalline molecular framework:small molecule compounds may include combining guanidinium cations, organosulfonate anions, and small molecules in a single step. The crystalline molecular framework:small molecule compounds can be used to determine the structure of the small molecule(s).

18 Claims, 30 Drawing Sheets

Scheme 1

Table 1

| No. | Host | Guest target | Space Group | Cell Parameters a, b, c (Å) | Cell Parameters (°) | Cell volume (Å$^3$) | $R_1$ | Flack parameter |
|---|---|---|---|---|---|---|---|---|
| 1A | G$_2$ADS | Guaiazulene | Pbca | 13.15, 12.78, 26.57 | 90, 90, 90 | 4463 | 0.0424 | N/A |
| 1B | G$_2$BPDS | Guaiazulene | Pbca | 13.89, 12.98, 24.76 | 90, 90, 90 | 4462 | 0.0575 | N/A |
| 2 | G$_2$NDS | Azulene | P2$_1$/n | 7.61, 21.40, 11.93 | 90, 90.75, 90 | 1942 | 0.0478 | N/A |
| 3 | G$_2$BPDS | 2,6-diisopropylaniline | P2$_1$2$_1$2$_1$ | 12.58, 13.96, 24.54 | 90, 90, 90 | 4312 | 0.0302 | 0.49(5) |
| 4 | GBPMS | S-(+)-Carvone | P2$_1$2$_1$2$_1$ | 7.51, 12.06, 25.59 | 90, 90, 90 | 2316 | 0.0336 | 0.02(3) |
| 5 | G$_2$NDS | (3aR)-(+)-Sclareolide | P2$_1$2$_1$2$_1$ | 12.87, 14.53, 18.54 | 90, 90, 90 | 3470 | 0.0448 | -0.07(4) |
| 6 | G$_2$NDS | Drospirenone | P1 | 12.13, 12.49, 14.26 | 92.66, 91.26, 116.19 | 1934 | 0.0649 | 0.03(5) |
| 7 | G$_2$BPDS | Progesterone | P2$_1$2$_1$2$_1$ | 11.27, 26.27, 27.80 | 90, 90, 90 | 8235 | 0.0797 | 0.08(4) |
| 8 | G$_2$SDS | 7-Acetyl-5,8-dihydroxy-4-isopropyl-1-methylbicyclo[4.3.0]nonane | P1 | 7.61, 12.02, 32.01 | 87.01, 86.31, 89.99 | 2918 | 0.0595 | 0.01(8) |
| 9 | G$_3$TSPHB | Isophorone/ Neryl acetate | P2$_1$2$_1$2$_1$ | 7.57, 24.67, 39.62 | 90, 90, 90 | 7403 | 0.0563 | 0.46 |
| 10 | G$_4$TSPB | Deacetylated pancuronium | C2 | 36.03, 19.83, 18.78 | 90, 117.72, 90 | 11877 | 0.0881 | 0.02(2) |

Figure 2

TRISULFONATES
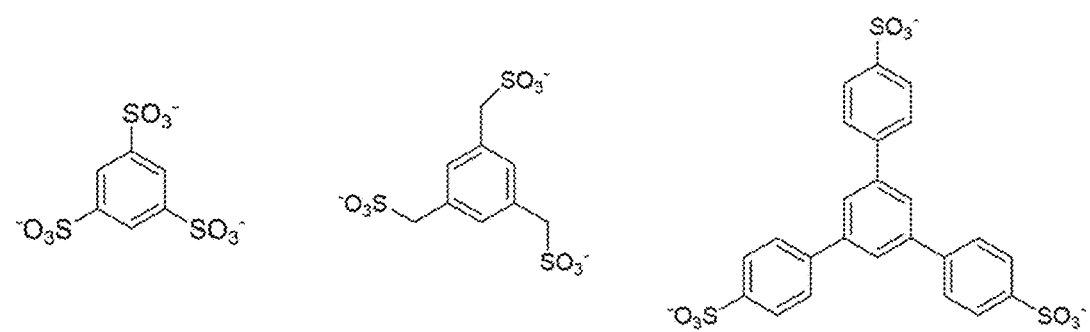
TETRASULFONATES
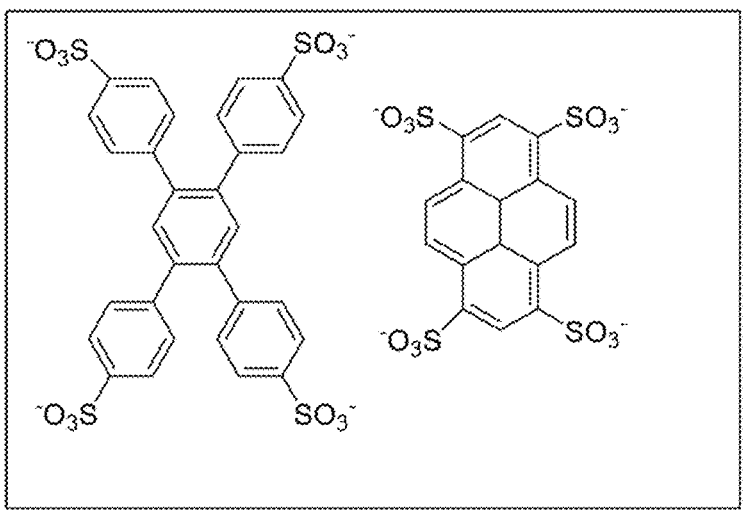
HEXASULFONATES
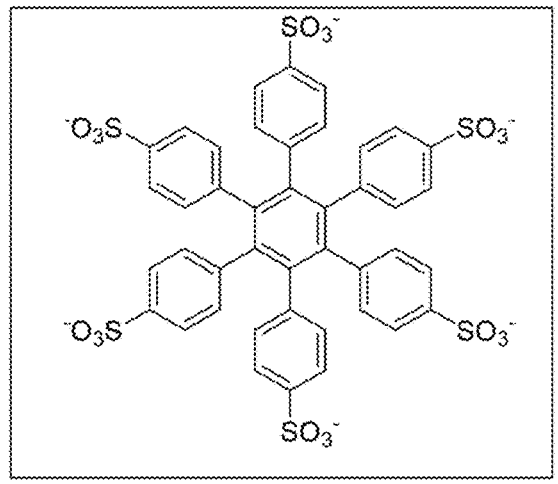
Figure 5

| Name Cpd/Sponge | Structure | Space group | Length x width | Occupancy | $R_1/wR_2$ |
|---|---|---|---|---|---|
| Isoprene /Zn | 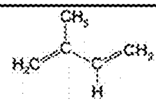 | C2/c | 3.6 3.2 | 0.6 | 0.0532/0.1664 |
| Guaiazulene (500 ng) /Zn | 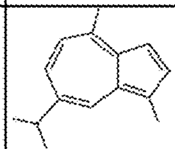 | C2/c | 5.1 6.7 | 0.6 later 1 | 0.0859/0.3021 Later 0.0379/0.1035 |
| Guaiazulene (80 ng) /Zn | | Cc | | 0.8 | 0.0993/0.3190 |
| 4-nitro benzaldehyde /Zn | 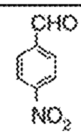 | C2/c | 2.4 5.7 | 0.5 later 1 | 0.1130/0.3380 Later 0.0667/0.2061 |
| 2,6-diisopropyl aniline /Zn | 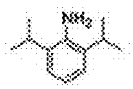 | C2/c | 7.4 4.2 | 0.76 later 1 | 0.1182/0.3520 Later 0.0653/0.1541 |
| Cinnamaldehyde /Zn | 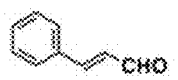 | C2/c | 7.6 2.7 | 0.5 later 1 | 0.0750/0.2631 Later 0.0416/0.1216 |
| Vanillin/Zn | 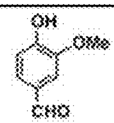 | P-1 | 5.5 4.7 | 2/2 | 0.1103/0.3402 Later 0.0733/0.2390 |
| 9-Bromophenanthrene /Zn | 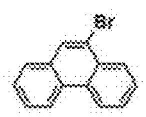 | C2/c | 6.9 5.3 | 0.68 later 0.63 | 0.1162/0.3753 Later 0.0752/0.2359 |
| Dimethyl 1,4-Cubanedicarboxylate /Zn | 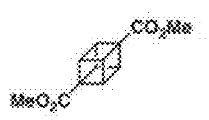 | P-1 | 9.7 2.2 | 0.7 later 1 | 0.1345/0.3775 Later 0.1296/0.4390 |
| Santonin/Zn | 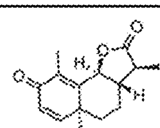 | $P2_1$ | 7.3 4.9 | 1 | 0.0827/0.1813 Later 0.0312/0.0781 |
| DDD/Zn | 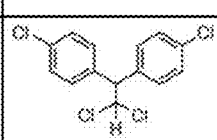 | C2/c | 10.1 2.7 | ? | 0.078/0.2736 |

Figure 6

| | | | | | |
|---|---|---|---|---|---|
| /Zn | | C2 | 7.8 4.1 | 3.79/4 | 0.0511/0.1396 |
| /Zn | | C2 | 10.8 4.8 | 2.8/4 | 0.0788/0.2259 |
| /Zn | | C2/c | 13.2 6.7 | 0.5 later 0.5 | 0.1065/0.2915 Later 0.0808/0.2136 |
| /Zn | | Cc | 13.2 8.4 | 0.5 later 0.6 | 0.0730/0.2184 Later 0.0536/0.1545 |
| /Zn | | C2/c | 13.2 8.4 | 0.94 later 1 | 0.0823/0.2283 Later 0.0768/0.1730 |
| Cycloelatanene A/Zn | | C2 | 13.3 4.9 | 0.47 | 0.0542/0.1894 |
| Cycloelatanene A/Zn | | C2 | 13.3 4.9 | 0.86/2 | 0.0340/0.0997 |
| Styrene ozonide/Zn | | C2/c | 6.3 5.1 | 0.37/0.42 /0.82 | 0.0633/0.1893 |
| Stilbene ozonide/Zn entered sponge at 4 °C | | C2/c | 9.9 3.0 | 0.71 cis 0.66 trans | 0.0553/0.1719 |
| Stilbene ozonide/Zn entered sponge at 50°C (benzoic acid) | | C2/c | 9.9 3.0 | 0.68 0.62 0.62 0.64 | 0.0699/0.2177 |
| Cyclopentene ozonide/Zn | | C2/c | 3.6 3.9 | 0.49 0.43 | 0.0949/0.2978 |

Figure 6 (cont.)

| | | | | | |
|---|---|---|---|---|---|
| Astellifadiene/Zn | | C2 | 11.2 6.7 | | 0.0341/0.1028 |
| Elatenyne/Zn | | C2 | 11.6 5.3 | | 0.0673/0.2136 |
| /Zn | | C2 | 19.1 3.1 | | 0.0426/0.1113 |
| MCE23 | | | | 0.242/0.258 | 0.0621/0.1951 |
| /Zn | | | | 0.25 | 0.0783/0.2110 |
| /Zn | | C2/c | 8.8 4.9 | | 0.0482/0.1489 |
| /Zn | | C2/c | | | 0.0725/0.2300 |
| /Zn | | C2/c | | | 0.0517/0.1364 |
| a-Humulene /Zn | | C2/c | 6.6 5.6 | 0.35 | 0.0539/0.1686 |
| /Zn | | C2/c | | | 0.0528/0.1592 |
| /Zn | | C2/c | | | 0.0556/0.1685 |

Figure 6 (cont.)

| | | | | |
|---|---|---|---|---|
| /Zn | (structure) | | 0.29/0.30 | 0.0606/0.1847 |
| /Zn | (structure) | | | 0.0624/0.2055 |
| /Zn | (structure) | | | 0.0436/0.1308 |
| /Zn | (structure) | | | 0.0397/0.1035 |
| /Zn | (structure) | | | 0.0725/0.2268 |
| /Zn | (structure) | | | 0.0483/0.1568 |
| TTF/Co | (structure) | Fm-3m | | 0.0998/0.2830 |
| Diphenylamine/Co | (structure) | P4$_2$/mnm | | 0.0853/0.2257 |
| /Zn | (structure) | C2 | | 0.0602/0.1749 |
| /Zn | (structure) | C2 | | 0.0742/0.2049 |
| /Zn | (S) (structure) | C2 | 0.94/2 | 0.0745/0.2548 |
| /Zn | (R) (structure) | C2 | 0.85/2 | 0.0978/0.3129 |

Figure 6 (cont.)

| | | | | | |
|---|---|---|---|---|---|
| /Zn | | P2₁2₁2₁ | | | 0.0588/0.1553 |
| /Zn | | P2₁2₁2₁ | | 1/0.77 | 0.0486/0.1383 |
| /Zn | | P2₁2₁2₁ | | | 0.0610/0.11739 |
| /Zn | | P2₁2₁2₁ | | 0.54 | 0.0879/0.2995 |
| /Zn | (S) | C2 | | 7.4 5.9 | 0.371/0.251 | 0.0749/0.2612 |
| /Zn | (R) | C2 | | 0.278/0.222 | 0.0598/0.2036 |
| /Zn | (S) | C2 | | 10.5 4.5 | 0.491 | 00651/0.2139 |
| /Zn | (R) | C2 | | 0.531 | 0.0580/0.1852 |
| Retinal/Zn | | | | 0.33~0.65 | 0.0684/0.1728 |

Figure 6 (cont.)

| | | | | | |
|---|---|---|---|---|---|
| /Zn | (R)-6 | P2₁2₁2₁ | | 1 | 0.0371/0.0885 |
| /Zn | (S)-6 | P2₁2₁2₁ | | 0.94 | 0.0386/0.1018 |
| /Zn | (R)-7 | P2₁2₁2₁ | | 0.82 | 0.0338/0.0846 |
| /Zn | (S)-7 | P2₁2₁2₁ | | 0.86 | 0.0496/0.1200 |
| /Zn | | C2/c | | 1/0.5 | 0.0811/0.2226 |
| /Zn | | C2/c | | 0.48/0.52 | 0.0371/0.1168 |
| /Zn | | C2/c | | 0.45/0.50 | 0.0408/0.1166 |
| /Zn | | C2/c | | 0.4/0.6 | 0.0945/0.2514 |
| /Zn | | C2/c | | 0.32/0.24 | 0.0833/0.3141 |
| /Zn | | C2/c | | 1 | 0.0726/0.2212 |
| /Zn | | C2/c | | 0.32/0.24 | 0.1174/0.3498 |
| /Zn | | C2/c | | 1/0.32 | 0.1054/0.3462 |

Figure 6 (cont.)

| | | | | | |
|---|---|---|---|---|---|
| /Zn | 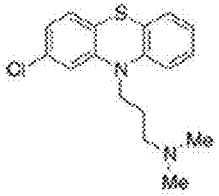 | C2/c | | 0.33/0.25 | 0.0896/0.2581 |
| /Zn | 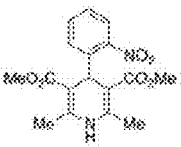 | C2/c | | 0.33/0.4 | 0.0833/0.2834 |
| /Zn | 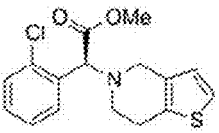 | P2$_1$/c | | 1 | 0.0982/0.3478 |
| /Zn | 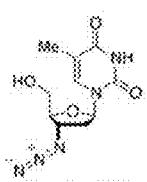 | C2 | | 0.47/0.53/ 0.47/0.53 | 0.0868/0.2506 |
| /Zn | 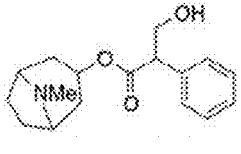 | P2$_1$ | | 1 | 0.1338/0.3521 |
| /Zn | 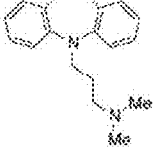 | C2/c | | 0.33 | 0.1128/0.3925 |
| /Zn | 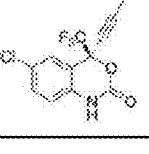 | C2 | | 0.2/0.167 | 0.1097/0.3453 |
Figure 6 (cont.)

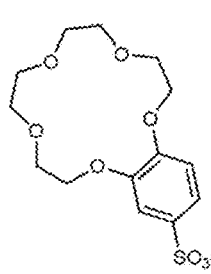
4-sulfobenzo-15-crown-5

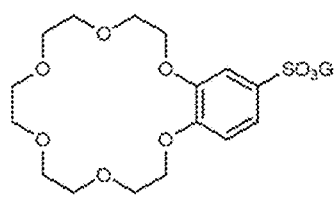
4-sulfobenzo-18-crown-6

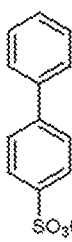
biphenyl-4-sulfonate

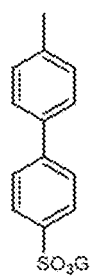
4-methyl-4'-biphenylsulfonate

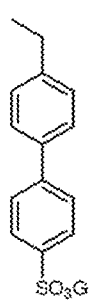
4'-ethylbiphenyl-4-sulfonate

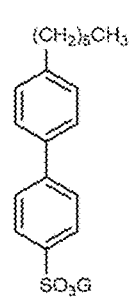
4'-hexylbiphenyl-4-sulfonate

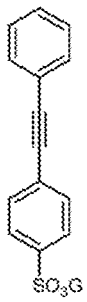
4-(phenylethynyl)benzenesulfonate

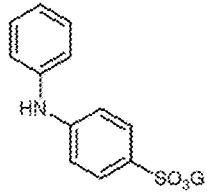
4-phenylamino-benzensulfonate

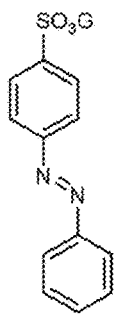
4-azobenzenesulfonate

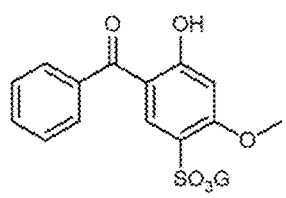
5-benzoyl-4-hydroxy-2-methoxybenzenesulfonate

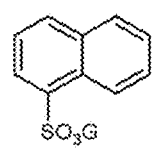
2-naphthalenesulfonate

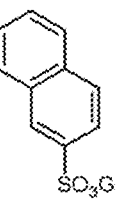
2-naphthalenesulfonate

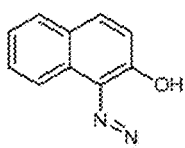
4-(2-hydroxy-napthalen-1-ylazo)napthalene-1-sulfonate

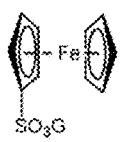
ferrocenesulfonate

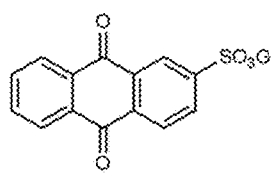
9,10-dioxo-9,10-dihydroanthracene-2-sulfonate

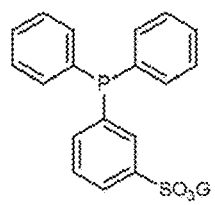
3-(diphenylphosphino)benzenesulfonate

Figure 8 (cont.)

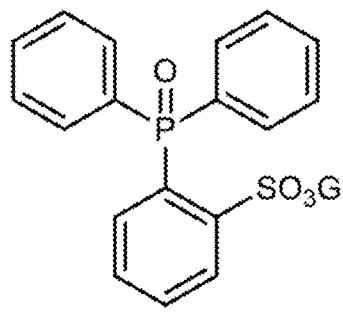
2-(diphenylphosphinoyl)benzenesulfonate

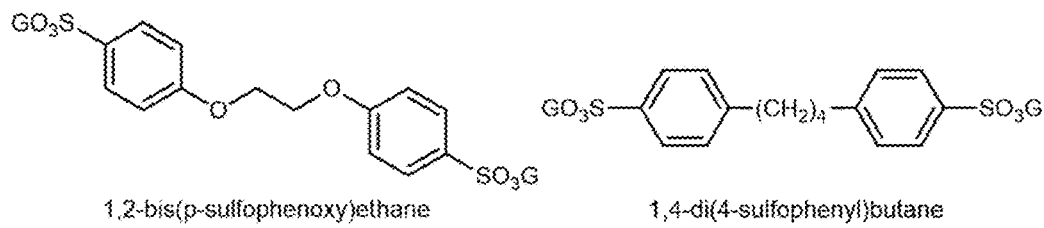
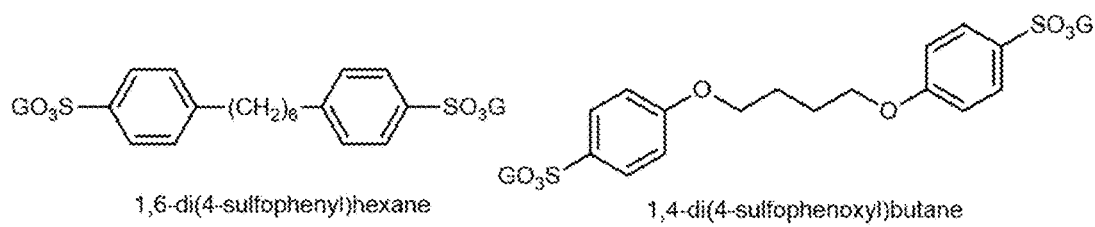
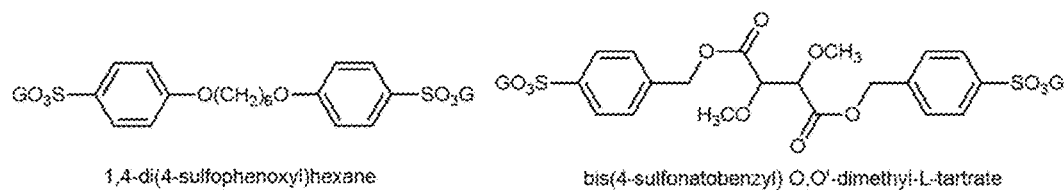
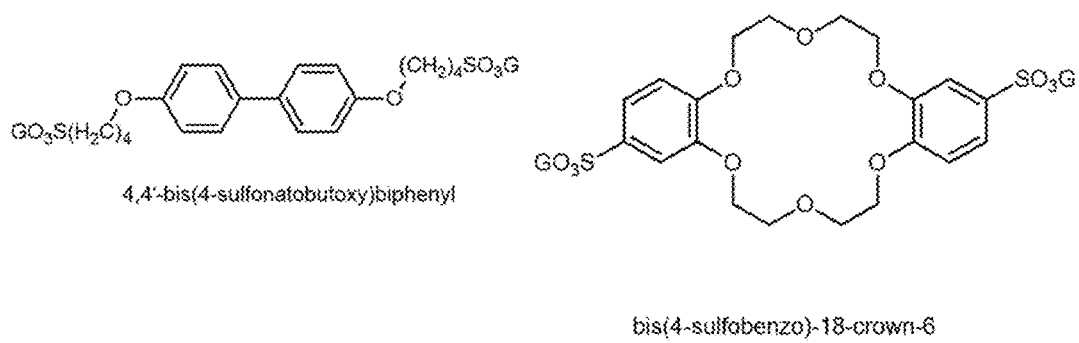
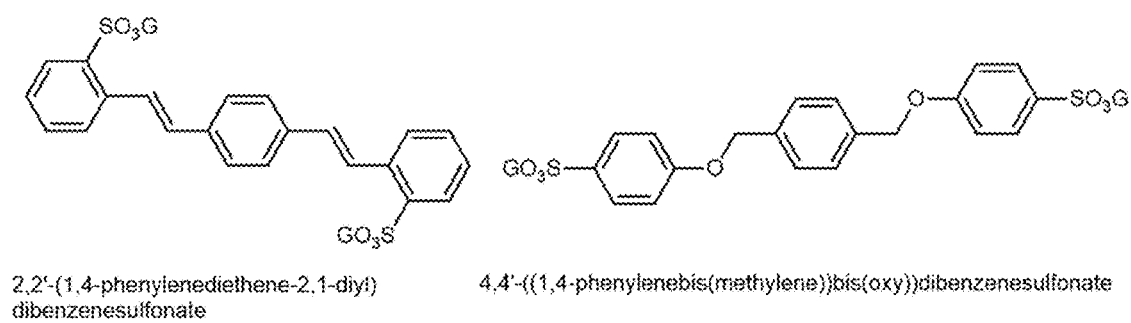
Figure 9 (cont.)

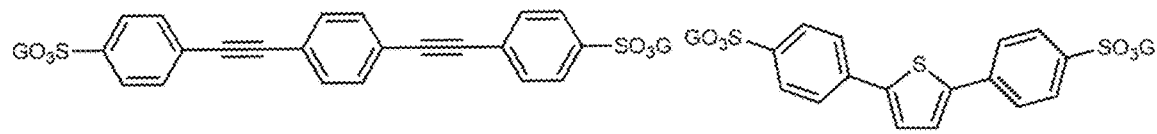
4,4'-(1,4-phenylenebis(ethyne-2,1-diyl))dibenzenesulfonate    2,5-di(4-sulfophenyl)thiophene
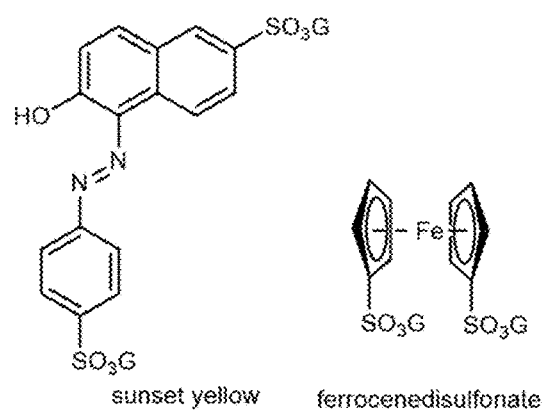
sunset yellow    ferrocenedisulfonate
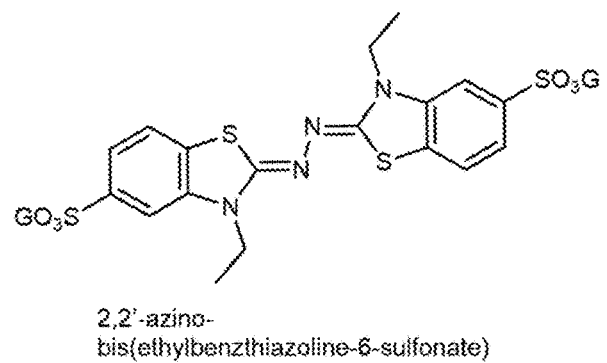
2,2'-azino-bis(ethylbenzthiazoline-6-sulfonate)
Figure 9 (cont.)

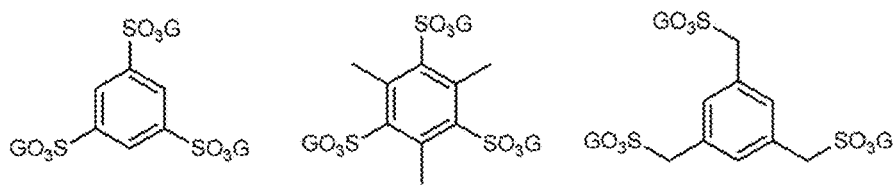
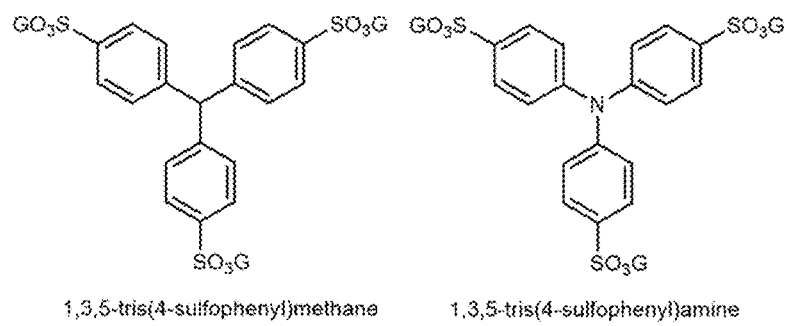
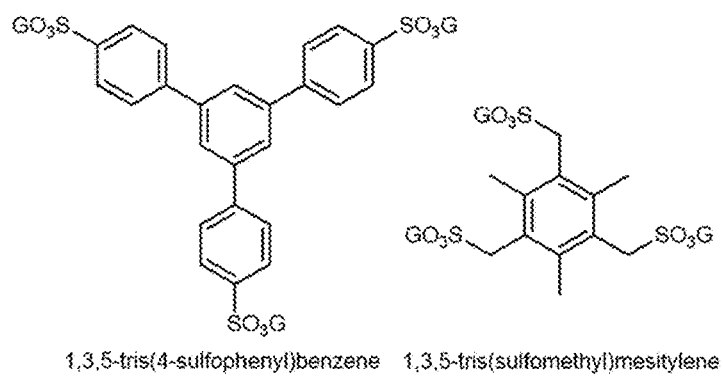
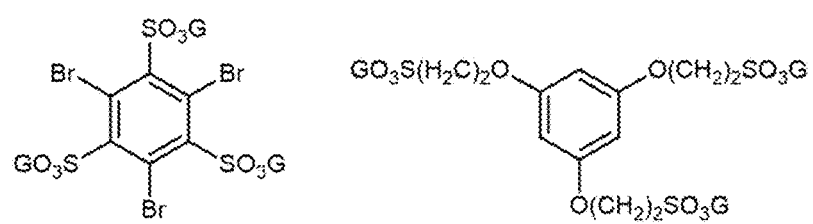
Figure 10

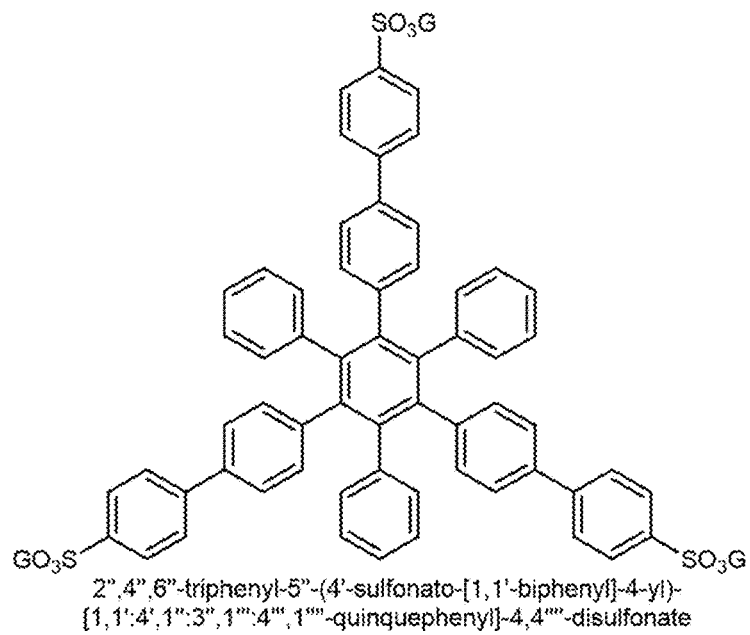
2",4",6"-triphenyl-5"-(4'-sulfonato-[1,1'-biphenyl]-4-yl)-
[1,1':4',1":3",1"':4"',1""-quinquephenyl]-4,4""-disulfonate
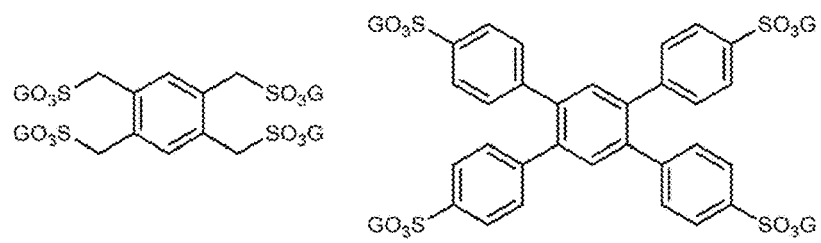
1,2,4,5-tetra(sulfonatomethylene)benzene     1,2,4,5-tetra(4-sulfophenyl)benzene
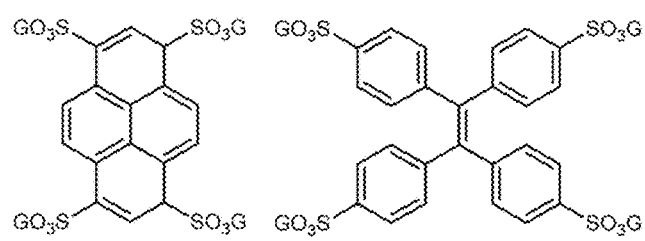
1,3,6,8-tetrasulfonato-pyrene    1,1,2,2-tetra(4-sulfophenyl)ethylene
Figure 10 (cont.)

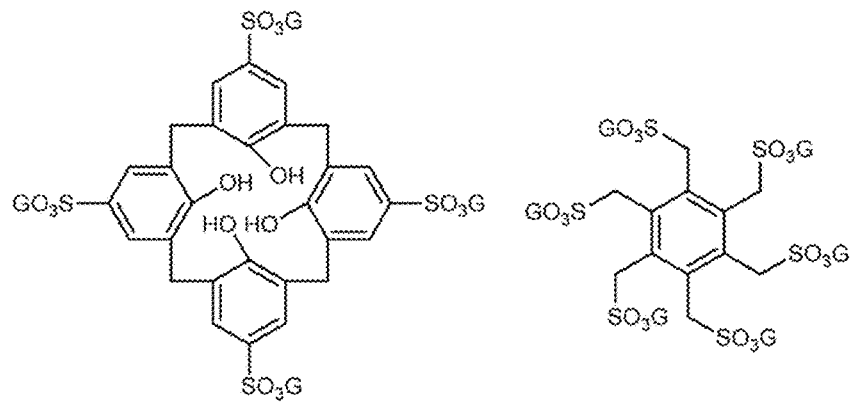
Calix[4]arenetetrasulfonate
1,2,3,4,5,6-hexa(sulfonatomethylene)benzene
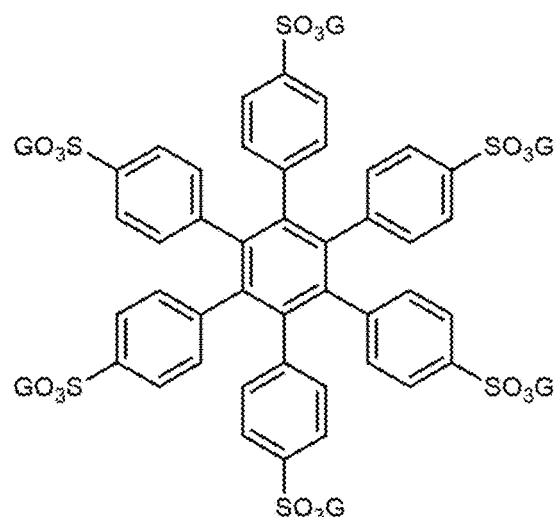
1,2,3,4,5,6-hexa(4-sulfophenyl)benzene
Figure 10 (cont.)

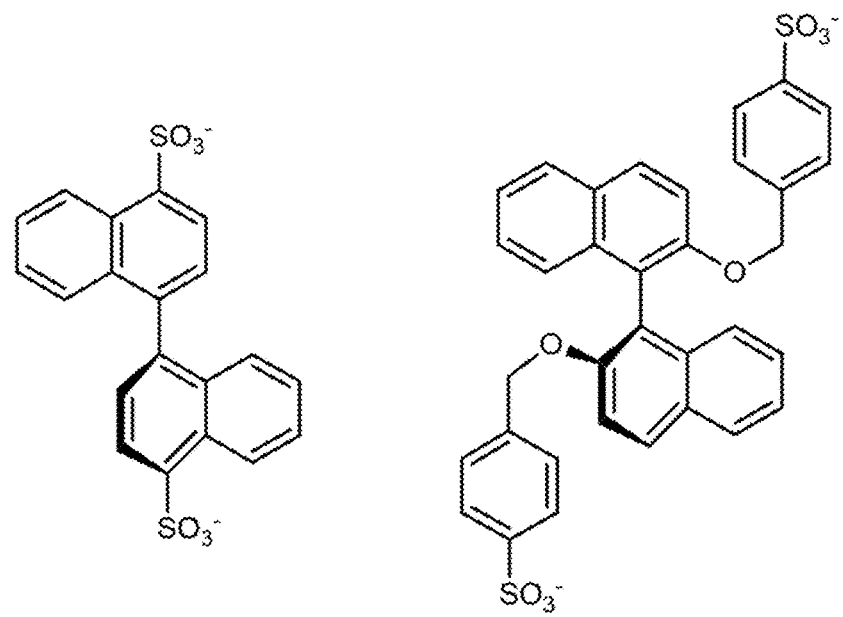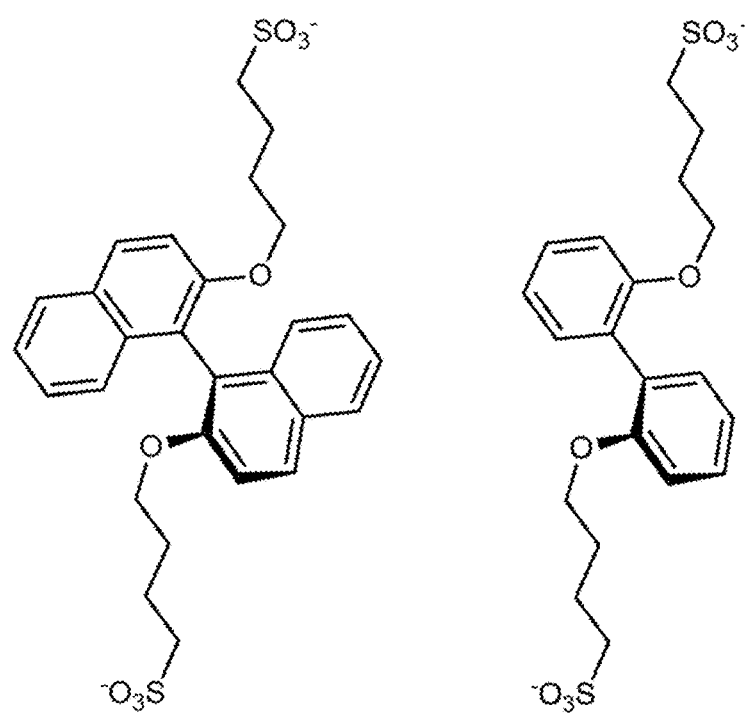
Figure 11 (cont.)

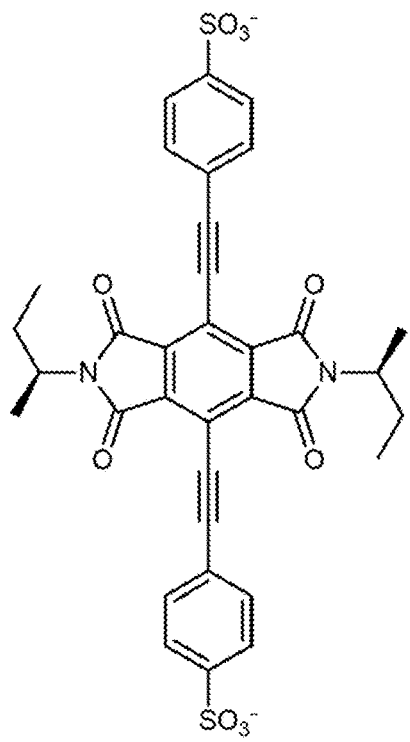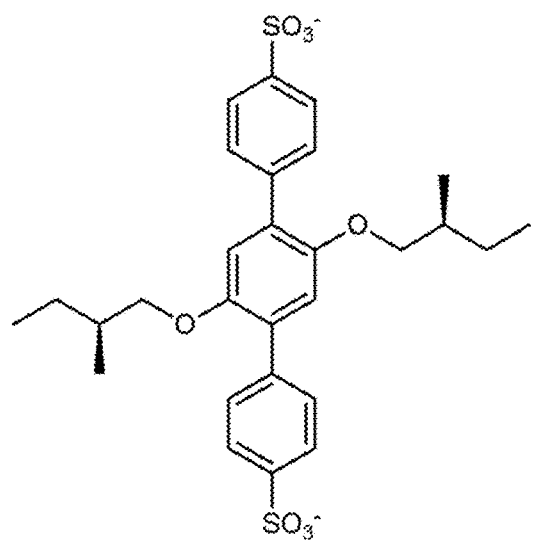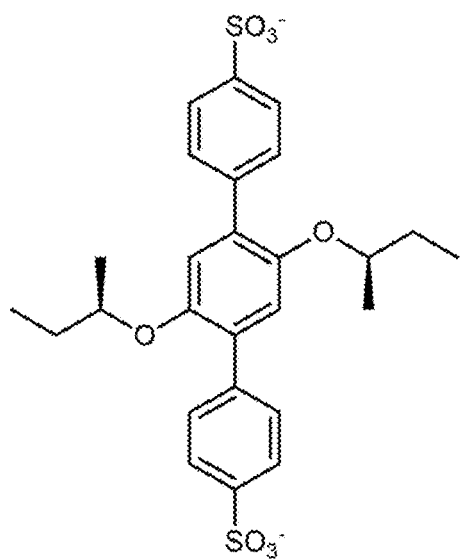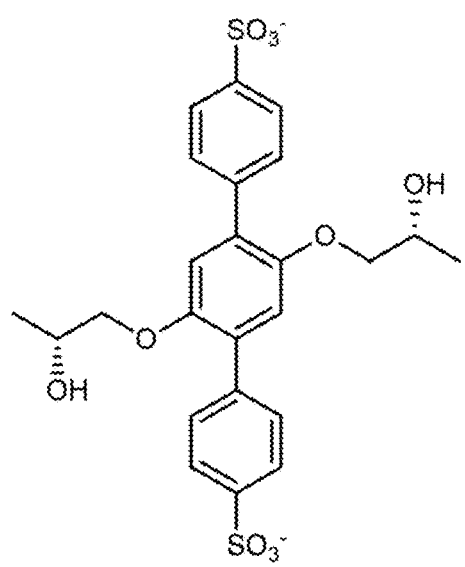
Figure 11 (cont.)

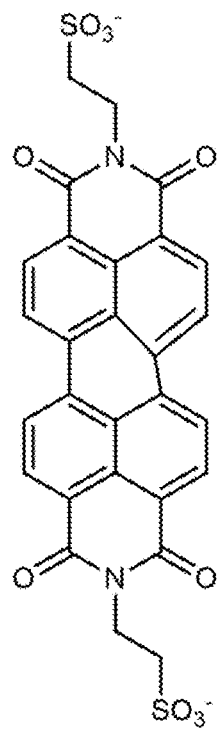
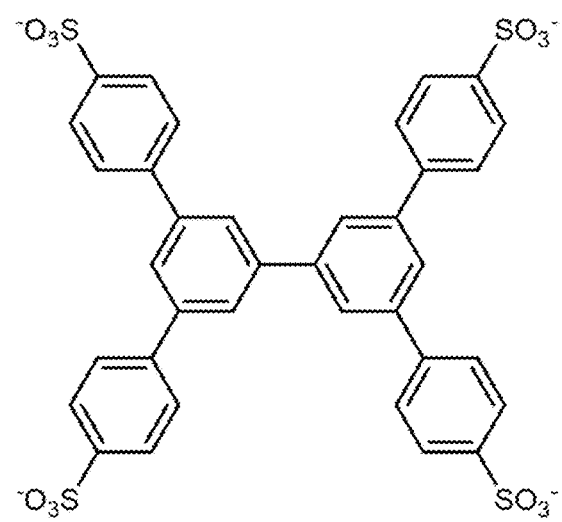
Figure 11 (cont.)

MOLECULAR HOST FRAMEWORKS AND METHODS OF MAKING AND USING SAME

CROSS REFERENCE TO RELATED APPLICATIONS

This application claims priority to U.S. Provisional Application No. 62/681,978, filed on Jun. 7, 2018, the disclosure of which is hereby incorporated by reference.

STATEMENT REGARDING FEDERALLY SPONSORED RESEARCH

This invention was made with government support under contract nos. 1308677 and 1400273 awarded by the National Science Foundation. The government has certain rights in the invention.

FIELD OF THE DISCLOSURE

The disclosure generally relates to self-assembled molecular host frameworks. More particularly, the disclosure relates to use of self-assembled molecular host frameworks in small molecule structure determination.

BACKGROUND OF THE DISCLOSURE

Determination of molecular structure by single crystal X-ray diffraction often can be frustrated by the inability to grow sufficiently large single crystals for conventional X-ray diffraction analysis, the tendency of many compounds to form oils or amorphous phases, low melting points that preclude solidification at convenient temperatures, and decomposition under ambient conditions. In the case of chiral molecules, insufficient anomalous scattering due to the absence of heavy atoms can preclude determination of absolute configuration of stereogenic centers. Other methods, such as circular dichroism, do not directly provide structural data unless potential structures are already confirmed. Although NMR spectroscopy, with the assistance of chiral derivatizing agents (CDAs), has been used for absolute configuration determination, many molecules have proven to be unsuitable for this analysis. Moreover, the method itself is often prone to errors. Compared to other frequently used methods, single-crystal X-ray diffraction remains the most definitive and reliable method for structure determination, despite the aforementioned technical limitations.

One strategy for the determination of the molecular structure of such "stubborn" target molecules relies on their inclusion in host frameworks that isolate and fix these molecules so they are amenable to X-ray analysis. This has been exemplified recently by absorption of target molecules into the cages consisting of metal organic host frameworks such as $\{[(Co(NCS)_2)_3(L)_4] \cdot x(solvent)\}_n$ and $\{[(ZnI_2)_3(L)_2] \cdot x(solvent)\}_n$ (L=tris(4-pyridyl)-1,3,5-triazine), which have been described as "crystalline sponges." By replacing the solvent guests and binding to the host framework through charge transfer, π-π, hydrogen bonds, or CH-π interactions to form a rigid conformation, the structure of target molecules was achieved using single-crystal X-ray diffraction. This approach has proven successful for absolute configuration determination of rather complicated natural products and synthetic molecules as well as reaction intermediates. Target molecules also have been trapped reactively by the chiral framework $Al_8(\mu-OH)_8(HCOO)_4(1,3,5\text{-benzenetribenzoate})_4$ by exchanging the formate ligands with carboxylate or hydroxyl groups on the targets. These examples rely on a "one size fits all" feature that has a certain attraction to users who are not practicing solid-state chemists, but this presents limitations as well. While the crystalline sponge approach can require only minute amounts of target compound, at this stage it is limited to only a few host frameworks and often requires specific intermolecular host-guest interactions or covalent fixation. Moreover, it can be hindered by slow absorption kinetics that can require weeks for complete target incorporation, an upper size limit on target molecules imposed by the size of the pore apertures, framework rigidity that cannot prevent disorder, and challenges in structure determination presented by low occupancy and retention of disordered solvent molecules in the space remaining in the sponge.

A convincing and convenient method for the determination of absolute configuration of stereogenic centers is single-crystal X-ray diffraction, but the technique is sometimes limited by difficulties in obtaining single crystals and by a lack of heavy atoms. Isolation and resolution of simple chiral guest molecules through co-crystallization has been previously explored. However, the determination of molecular structures through inclusion remains undeveloped.

Based on the foregoing, there exists an ongoing and unmet need for improved frameworks for structure determination and adding to the characterization arsenal available for structure determination.

SUMMARY OF THE DISCLOSURE

The present disclosure provides molecular frameworks (e.g., guanidinium sulfonate molecular frameworks), small molecule crystalline compounds comprising the molecular frameworks, and uses of the molecular frameworks and small molecule crystalline compounds.

In an aspect, the present disclosure provides molecular frameworks (e.g., guanidinium sulfonate molecular frameworks). The molecular frameworks can be used to form small molecule crystalline compounds, which may be used in structure determination methods such as, for example, structure determination methods disclosed herein. In various examples, a guanidinium sulfonate molecular framework, which may be a molecular host, comprises, consists essentially of, or consists of a plurality of guanidinium cations and a plurality of organosulfonate anions (e.g., organomonosulfonate anions and organopolysulfonate anions such as for example, organodisulfonate anions, organotrisulfonate anions, organotetrasulfonate anions, organopentasulfonate anions, organohexasulfonate anions, and the like), wherein the guanidinium cations and organosulfonate anions are associated via one or more hydrogen bonds.

In an aspect, the present disclosure provides crystalline molecular host:small molecule guest compounds. The compounds may be referred to as inclusion compounds or inclusion complexes. The molecular host is a molecular framework disclosed herein. The small molecule guest(s) is/are encapsulated by the molecular host. In various examples, a compound is formed by a method of the present disclosure (e.g., a single-step crystallization from a suitable solvent). A crystalline molecular host:small molecule guest compounds may be in the form of a single crystal. A compound can comprise various molecular hosts. A molecular host may be chiral. In an example, the molecular host and small molecule(s) are both chiral.

In an aspect, the present disclosure provides methods of making a crystalline molecular host:small molecule compound. A method can be used to make a crystalline molecular host:small molecule compound of the present disclosure. In various examples, a method is a single-step crystallization.

In an aspect, the present disclosure provides uses of crystalline molecular host:small molecule compounds. For example, a method of structure determination uses a crystalline molecular host:small molecule compound of the present disclosure.

Crystalline molecular host:small molecule compounds can be used in various structure determination methods. The methods can provide the structure of the molecular host and/or the small molecule. In certain examples, the methods provide the relative stereochemistry and/or absolute configuration of the molecular host and/or the small molecule.

BRIEF DESCRIPTION OF THE FIGURES

For a fuller understanding of the nature and objects of the disclosure, reference should be made to the following detailed description taken in conjunction with the accompanying figures.

FIG. 2. Table 1 showing crystallographic data for crystalline inclusion compounds.

FIG. 5. Examples of organotrisulfonate, organotetrasulfonate, and organohexasulfonate compounds.

FIG. 6. Examples of structure determination using prior art methods for comparison with the instant methods.

FIG. 10. Examples of guanidinium oligosulfonates. G is a guanidinium cation. The word "guanidinium" is removed in each chemical name.

DETAILED DESCRIPTION OF THE DISCLOSURE

Figure 1:
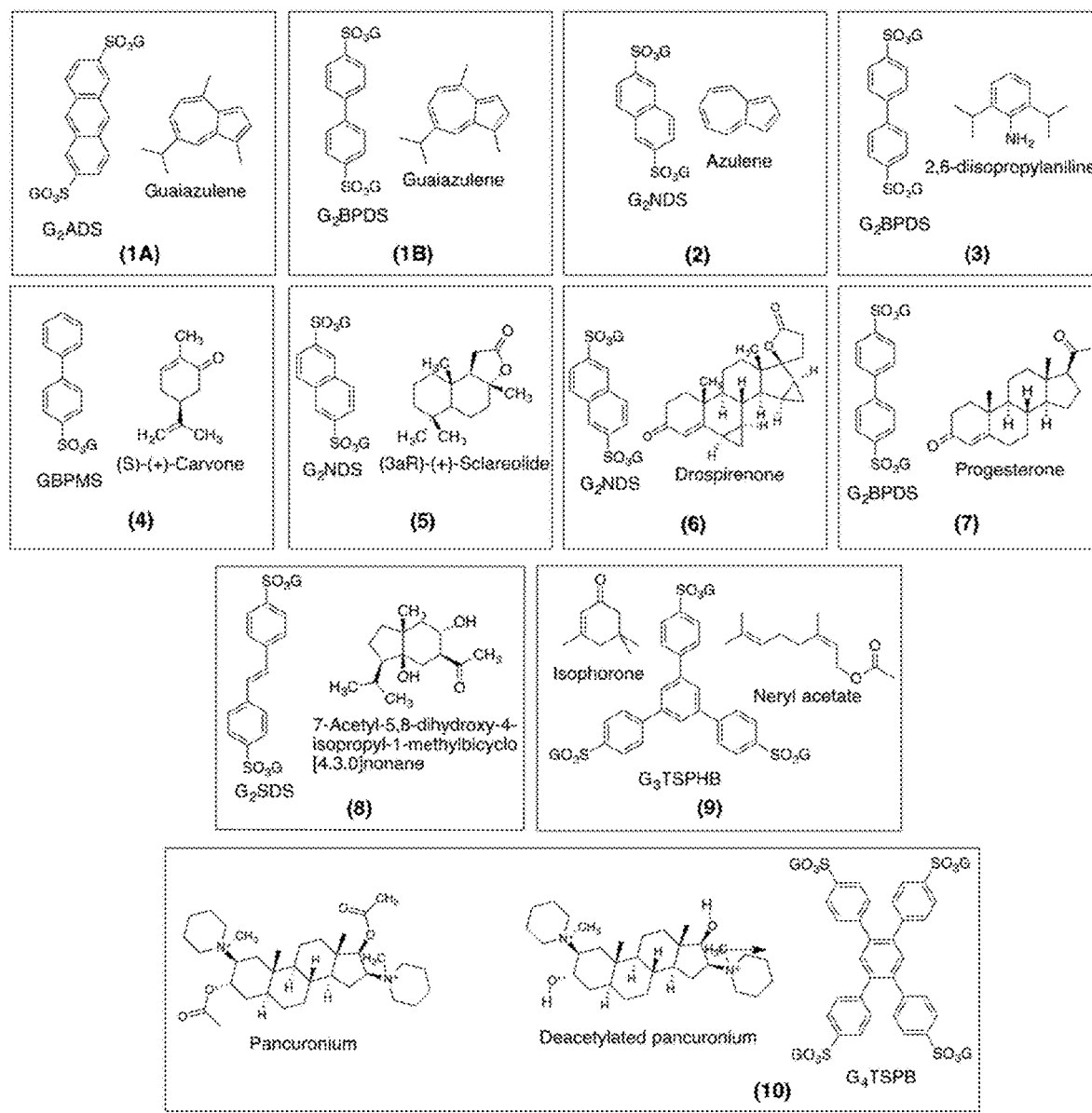
FIG. 1. Scheme 1 showing combinations of guanidinium sulfonate framework components and encapsulated target guest molecules that form single crystals amenable to single crystal X-ray diffraction, with determination of absolution configuration for examples with stereogenic centers.

Although claimed subject matter will be described in terms of certain embodiments and examples, other embodiments and examples, including embodiments and examples that do not provide all of the benefits and features set forth herein, are also within the scope of this disclosure. Various structural, logical, and method step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range. As an illustrative example, any range provided herein includes all values that fall within the ranges to the tenth decimal place, unless indicated otherwise.

The present disclosure provides molecular frameworks (e.g., guanidinium sulfonate molecular frameworks), small molecule crystalline compounds comprising the molecular frameworks, and uses of the molecular frameworks and small molecule crystalline compounds.

As used herein, unless otherwise stated, the term "group" refers to a chemical entity that has one terminus that can be covalently bonded to other chemical species. Examples of groups include, but are not limited to:

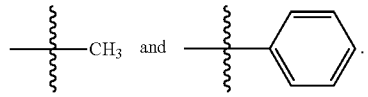

As used herein, unless otherwise stated, the term "moiety" refers to a chemical entity that has two or more termini that can be covalently bonded to other chemical species. Examples of moieties include, but are not limited to:

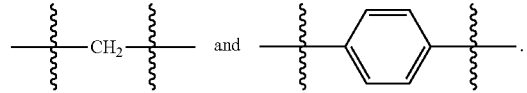

As used herein, unless otherwise indicated, the term "alkyl group" or "alkyl moiety" refers to branched or unbranched, linear saturated hydrocarbon groups/moieties and/or cyclic hydrocarbon groups/moieties. Examples of alkyl groups/moieties include, but are not limited to, methyl groups/moieties, ethyl groups/moieties, propyl groups/moieties, butyl groups/moieties, isopropyl groups/moieties, tert-butyl groups/moieties, cyclopropyl groups/moieties, cyclopentyl groups/moieties, cyclohexyl groups/moieties, and the like. Alkyl groups/moieties are saturated groups/moieties, unless it is a cyclic group/moiety. For example, the alkyl groups/moieties are a $C_1$ to $C_{30}$ alkyl group/moiety, including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$). The alkyl group/moiety may be unsubstituted or substituted with one or more substituent. Examples of substituents include, but are not limited to, substituents such as, for example, halogens (—F, —Cl, —Br, and —I), aliphatic groups (e.g., alkyl groups, alkenyl groups, alkynyl groups, and the like), halogenated aliphatic groups (e.g., trifluoromethyl group), aryl groups, halogenated aryl groups, alkoxide groups, amine groups, cyano groups, nitro groups, sulfur-containing groups (e.g., thiol groups, sulfate groups, sulfonic acid groups, sulfonate groups, and the like), carboxylate groups, carboxylic acids, ether groups, alcohol groups, alkyne groups (e.g., acetylenyl groups and the like), and the like, and combinations thereof. Alkyl group/moieties may further comprise one or more stereogenic center.

As used herein, unless otherwise indicated, the term "aryl group" or "aryl moiety" refers to $C_5$ to $C_{36}$, including all integer numbers of carbons and ranges of numbers of carbons therebetween (e.g., $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, and $C_{36}$), aromatic or partially aromatic carbocyclic groups/moieties. The aryl groups/moieties can comprise polyaryl moieties such as, for example, fused ring or biaryl moieties. The aryl group/moiety may be unsubstituted or substituted with one or more substituent. Examples of substituents include, but are not limited to, substituents such as, for example, halogens (—F, —Cl, —Br, and —I), aliphatic groups (e.g., alkyl groups, alkenyl groups, alkynyl groups, and the like), halogenated aliphatic groups (e.g., trifluoromethyl group), aryl groups, halogenated aryl groups, alkoxide groups, amine groups, cyano groups, nitro groups, sulfur-containing groups (e.g., thiol groups, sulfate groups, sulfonic acid groups, sulfonate groups, and the like), carboxylate groups, carboxylic acids, ether groups, alcohol groups, alkyne groups (e.g., acetylenyl groups and the like), and the like, and combinations thereof. Aryl group/moieties may further comprise one or more stereogenic center.

The present disclosure provides, in various examples, self-assembling molecular frameworks that can readily form inclusion compounds with target molecules (also referred to as small molecules), which may have complex structures, including, but not limited to, those with one or more stereogenic centers, as guests, through single-step crystallization rather than relying on diffusion of the target molecule into a crystalline sponge. For example, two-dimensional quasihexagonal hydrogen-bonded networks of guanidinium (G) and various organosulfonates (S) are capable of encapsulating a wide range of guests through single-step crystallization. Numerous organosulfonates are readily available through conventional organic synthesis protocols, permitting selection of an organosulfonate capable of accommodating the steric needs of the target molecule. The size, shape, dimensionality and physicochemical character of inclusion cavities in GS frameworks from guanidinium cations (G) and organosulfonate anions (S) can be adjusted readily through selection of appropriate organosulfonate components, enabling encapsulation of a wide range of target molecules. The GS frameworks are inherently flexible, allowing the framework to "shrink-wrap" around target molecules to achieve dense packing, which can minimize the occurrence of disorder, and reduce or eliminate inclusion of solvent molecules. Unlike the crystalline sponge method, which relies on diffusion, target molecules may be encapsulated in the GS host frameworks through a single-step co-crystallization process. Moreover, there are many examples of GS frameworks that are soluble in a range of polar solvents (e.g., water, methanol, DMF, acetonitrile, DMSO, and the like, and combinations thereof) that are compatible with target molecules, obviating a limitation of the crystalline sponge method, which requires the use of non-polar solvents, which may contain a small amount of a polar solvent. These characteristics permit X-ray structure determination of encapsulated targets with complex structures by refinement of the X-ray diffraction data using customary methods, and the existence of a heavy sulfur atom in the host framework provides anomalous X-ray dispersion that assists in determination of, for example, the absolute configuration of stereogenic centers in the encapsulated target, which can mitigate one or more challenges in determining absolute configuration of chiral centers in molecules consisting of light atoms (e.g., atoms with an atomic number (z) less than or equal to 8).

In an aspect, the present disclosure provides molecular frameworks (e.g., guanidinium sulfonate molecular frameworks). The molecular frameworks can be used to form small molecule crystalline compounds (e.g., crystalline molecular host:small molecule guest compounds), which may be used in structure determination methods such as, for example, structure determination methods disclosed herein.

In various examples, a guanidinium sulfonate molecular framework, which may be a molecular host, comprises, consists essentially of, or consists of a plurality of guanidinium cations and a plurality of organosulfonate anions (e.g., organomonosulfonate anions and organopolysulfonate anions such as for example, organodisulfonate anions, organotrisulfonate anions, organotetrasulfonate anions, organopentasulfonate anions, organohexasulfonate anions, and the like), where the guanidinium cations and organosulfonate anions are associated via one or more hydrogen bonds.

In various examples, a molecular framework has the following structure: $(C(NH_2)_3^+)_x[R—(SO_3^-)_z]_y$, where R is an organic group described herein, where z may have values of 1, 2, 3, 4, 5, 6, or greater, and x=yz (e.g., for the standard framework y=1 such that $(C(NH_2)_3^+)_x(R—(SO_3^-)_z)$, e.g., $(C(NH_2)_3^+)_x(^-O_3S—R—SO_3^-)y$, where x=2, z=2 and y=1).

Typically, the hydrogen-bonding motif of a molecular framework has a standard form, but it may also have other forms. Generally, there is at least one hydrogen bond in the molecular framework. In various examples, a hydrogen bond is formed by a bridging species, for example guanidinium-water-sulfonate or possibly even the guest may be part of a bridging species. In these examples, the framework could be termed non-standard.

A molecular framework may comprise one or more compensating cations, which may be charge compensating cations, (e.g., sodium ion(s), ammonium ion(s), and the like) and/or one or more compensating anions, which may be charge compensating cations, (e.g., sulfonate ion(s), phosphonate ion(s), sulfate ion(s), chloride ion(s) and the like). A molecular framework comprising one or more charge compensating cations and/or one or more compensating anions is charge neutral (electroneutral). Combinations of compensating cations (e.g., charge compensating cations) and/or compensating anions (e.g., charge compensating anions) may be used.

Figure 3:
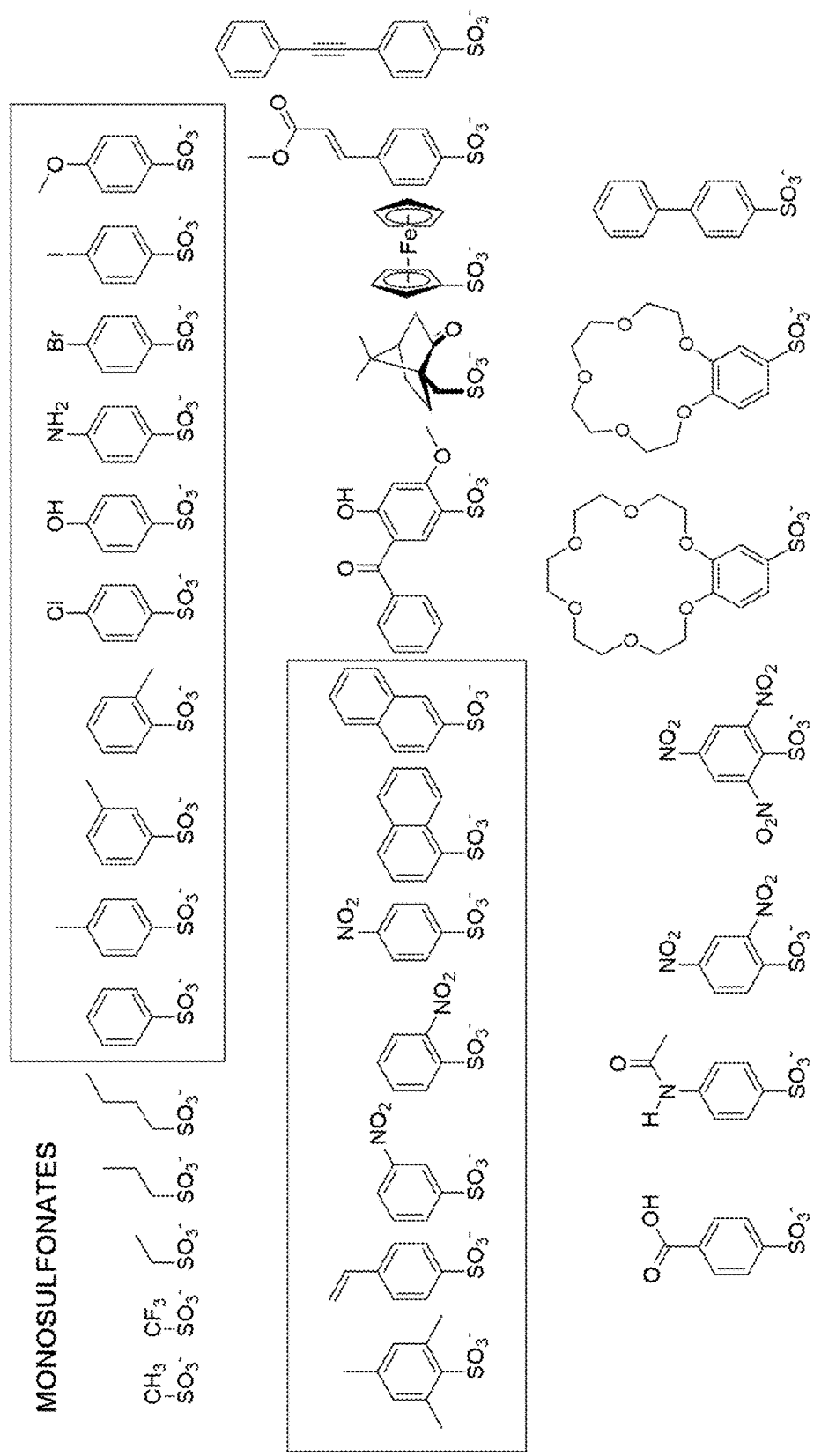
FIG. 3. Examples of organomonosulfonate compounds.
Figure 4:
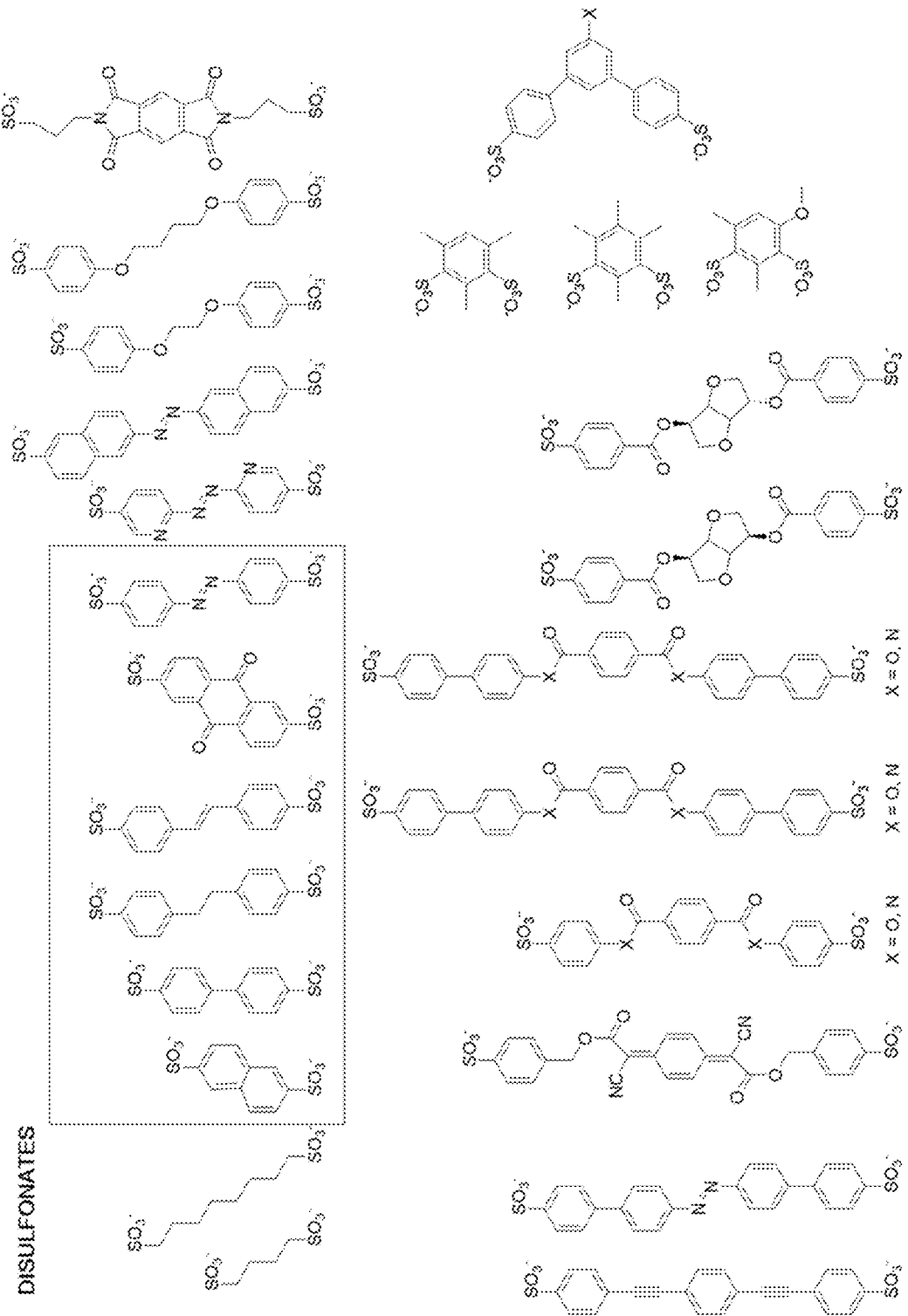
FIG. 4. Examples of organodisulfonate compounds.
Figure 7:
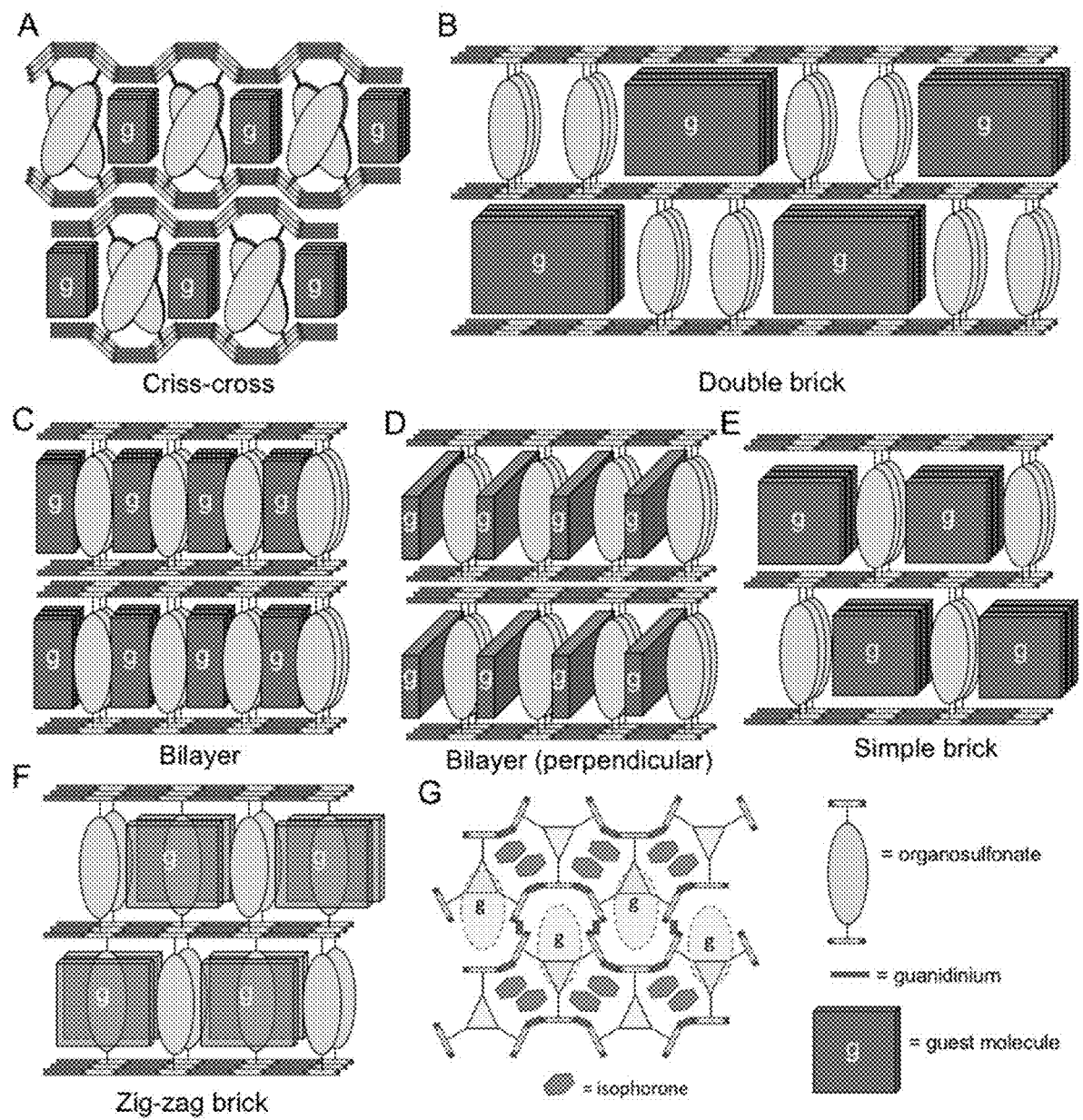
FIG. 7. Schematic representations of examples of common guanidinium disulfonate (GDS) architectures illustrating their desirable ability to accommodate guests with various sizes and shapes but with retention of the hydrogen-bonded GS network, to which the disulfonate "pillars" are attached. The pillars arrange into various topologies, as described by up-down arrangements about each sheet, directed by the size and shape requirements of the guest. Guanidinium monosulfonate (GMS) inclusion compounds also adopt many of these same topologies.
Figure 8:
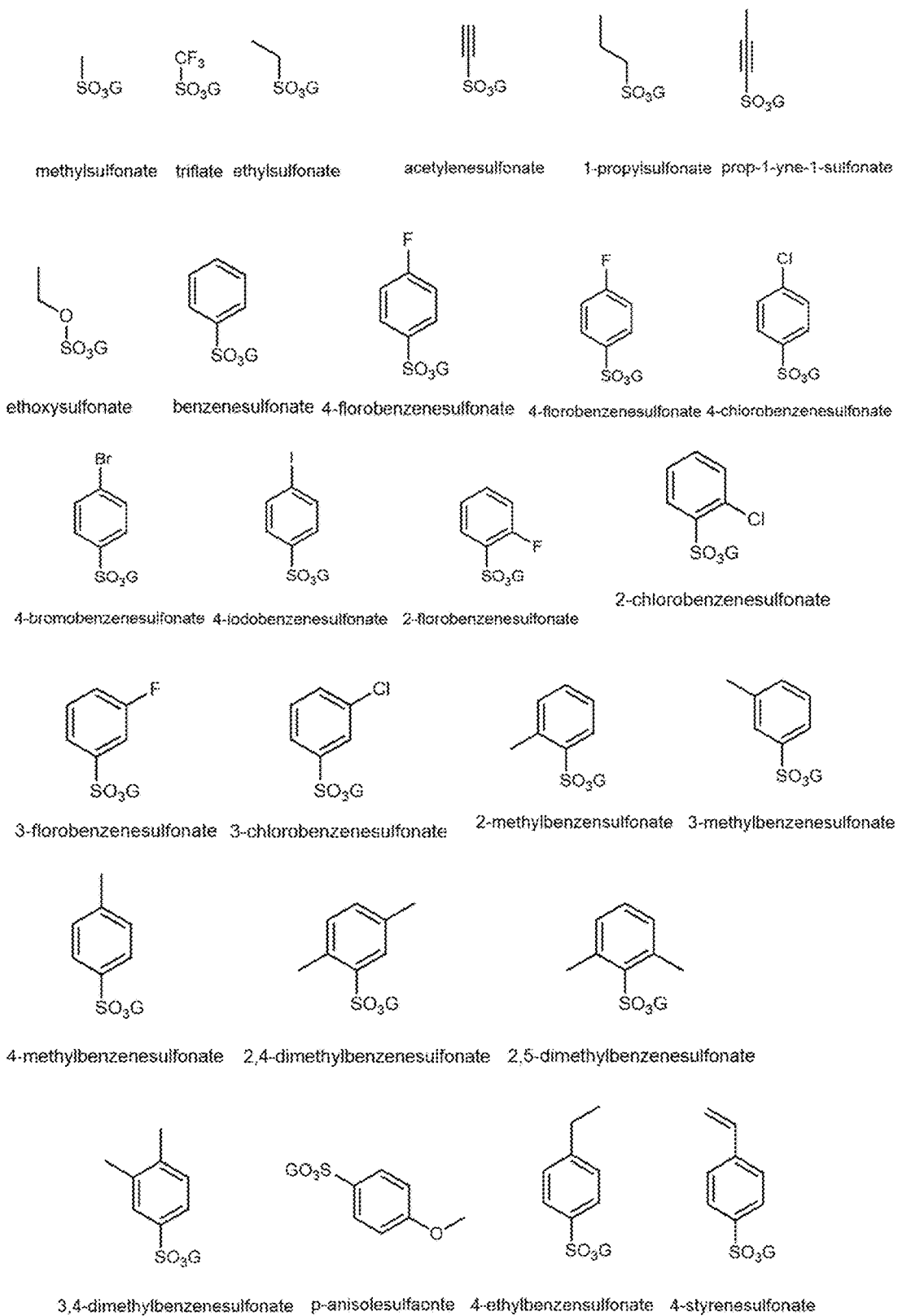
FIG. 8. Examples of guanidinium monosulfonates (GMSs). G is a guanidinium cation. The word "guanidinium" is removed in each chemical name.
Figure 8:
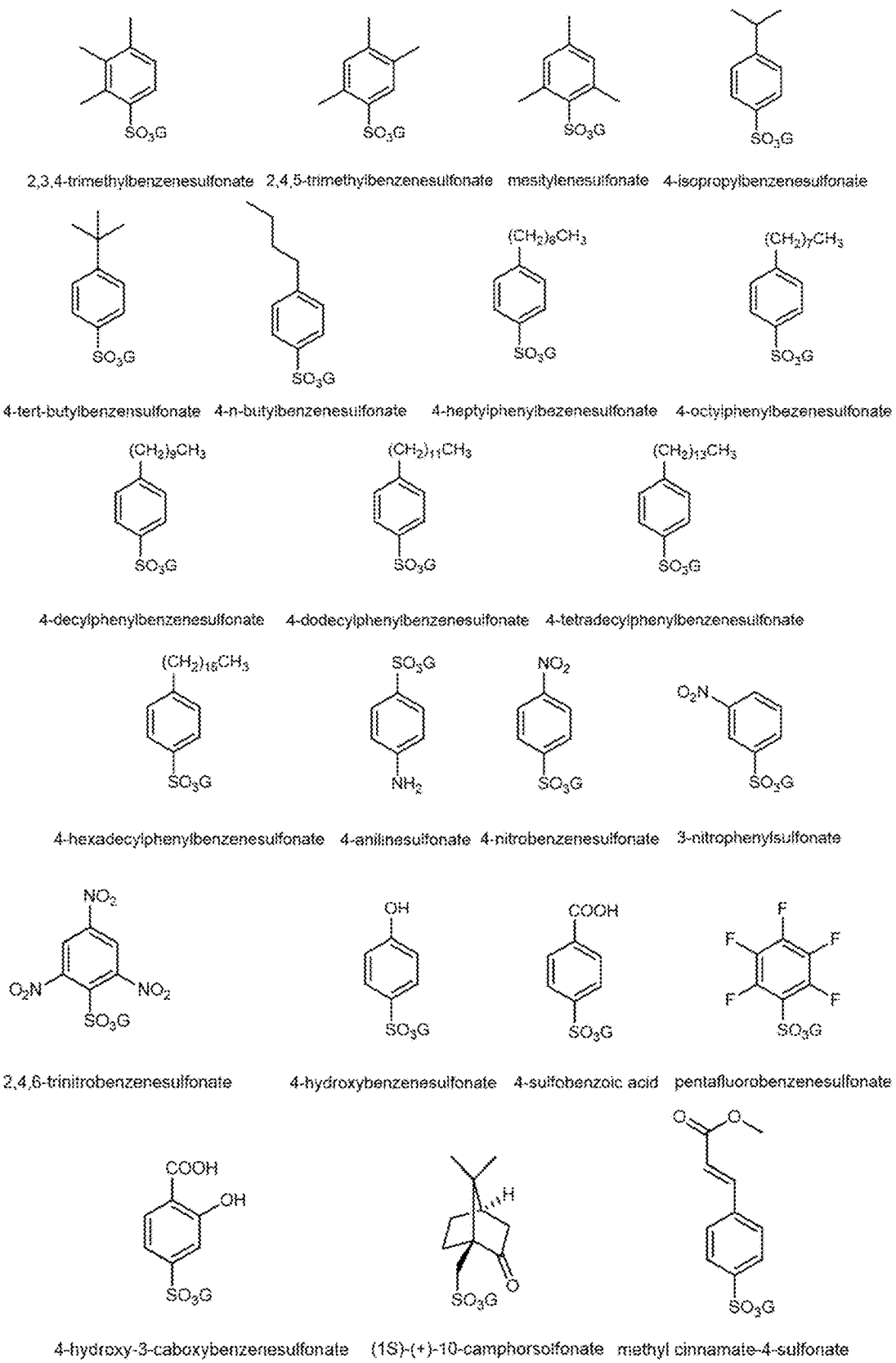
Figure 9:
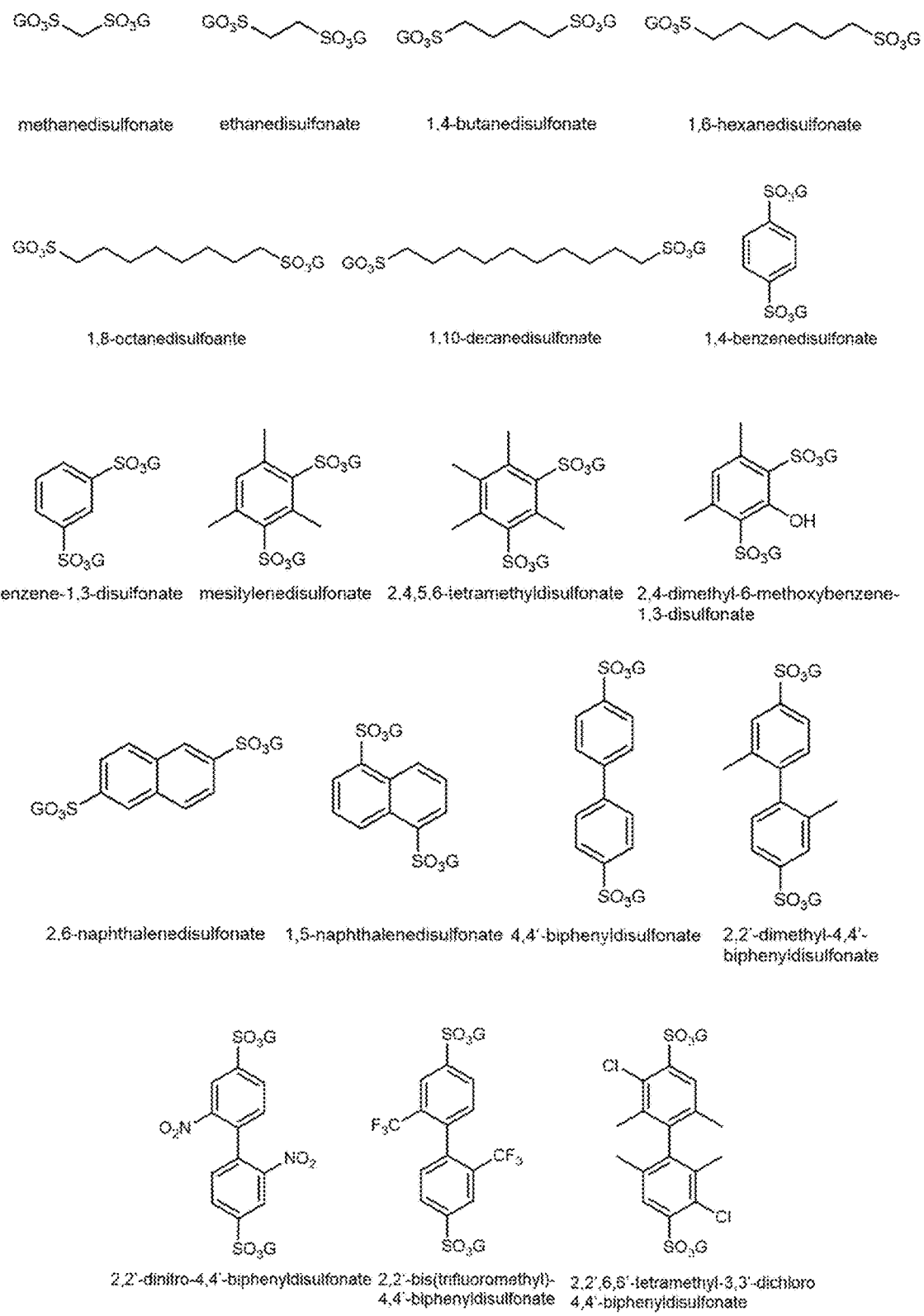
FIG. 9. Examples of guanidinium disulfonates (GDSs). G is a guanidinium cation. The word "guanidinium" is removed in each chemical name.
Figure 9:
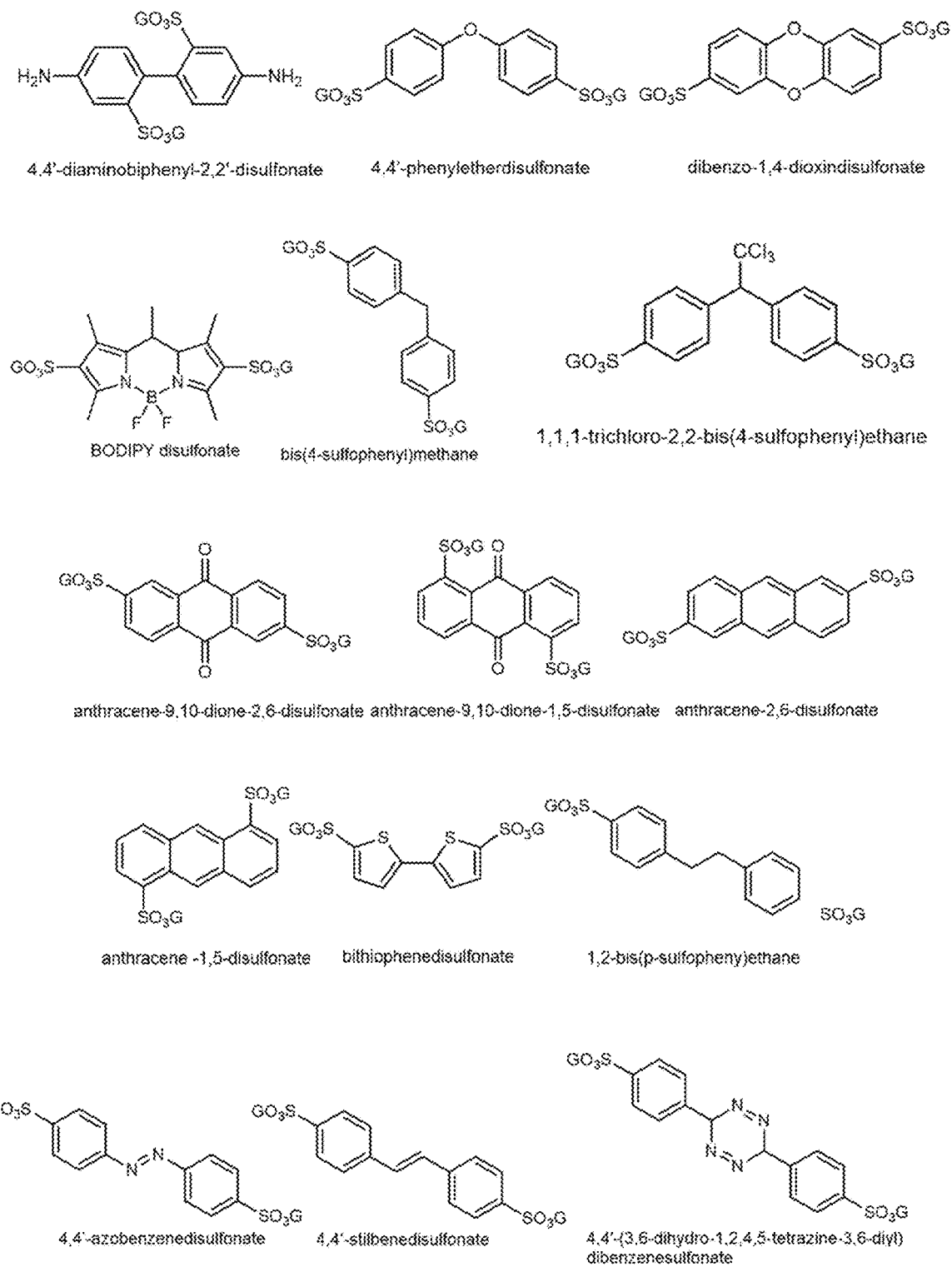
Figure 11:
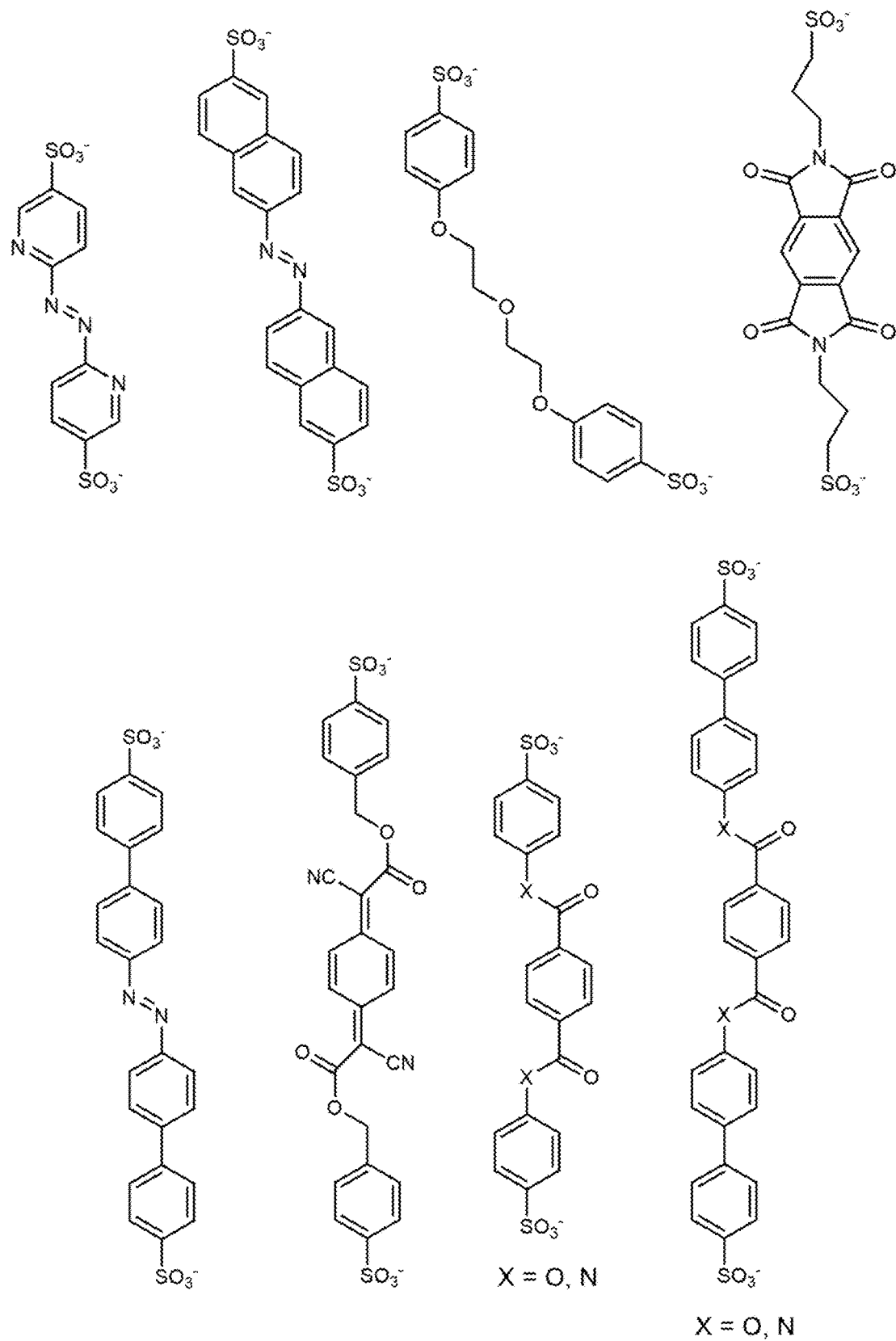
FIG. 11. Examples of organosulfonates.
Figure 11:
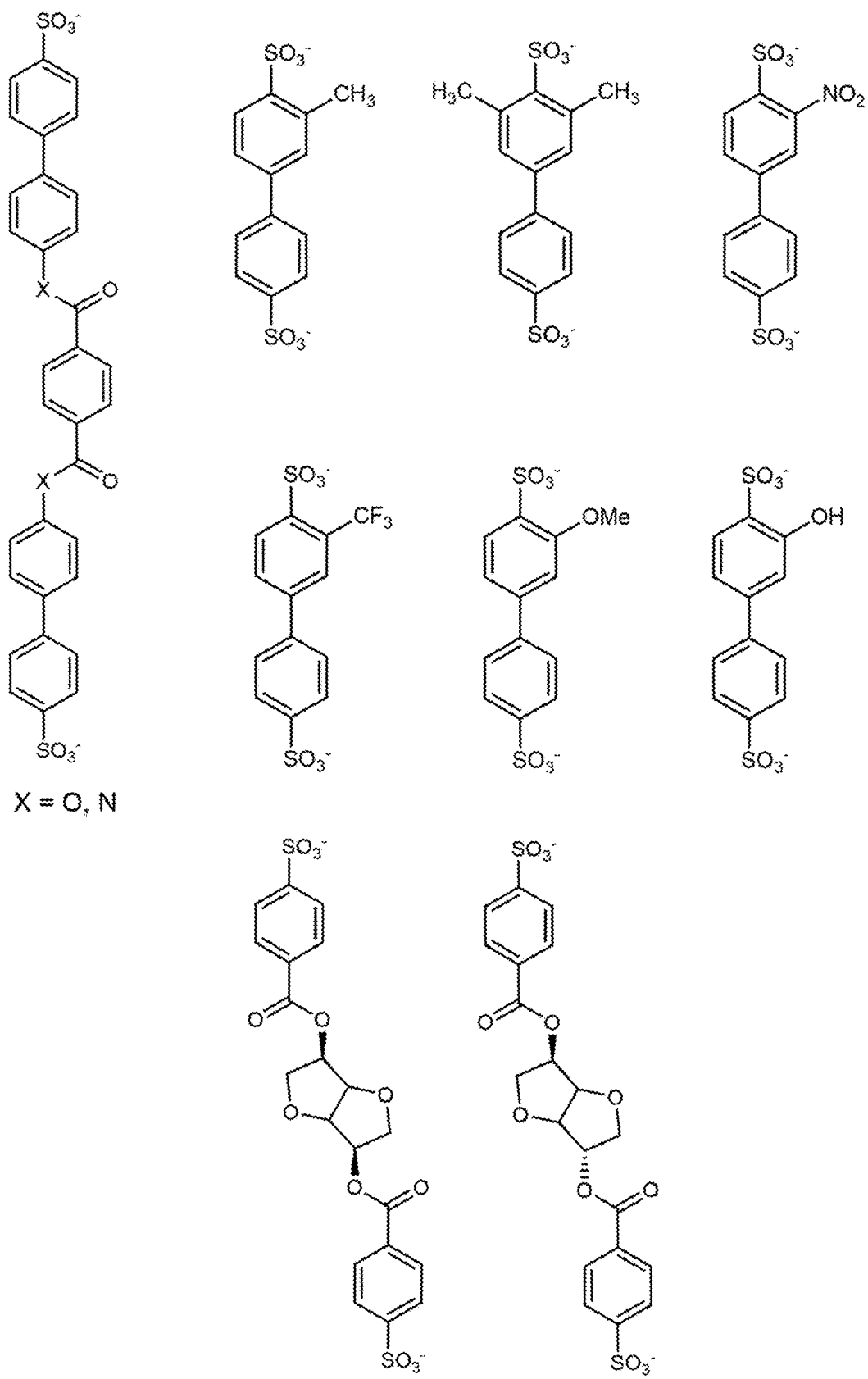
Figure 11:
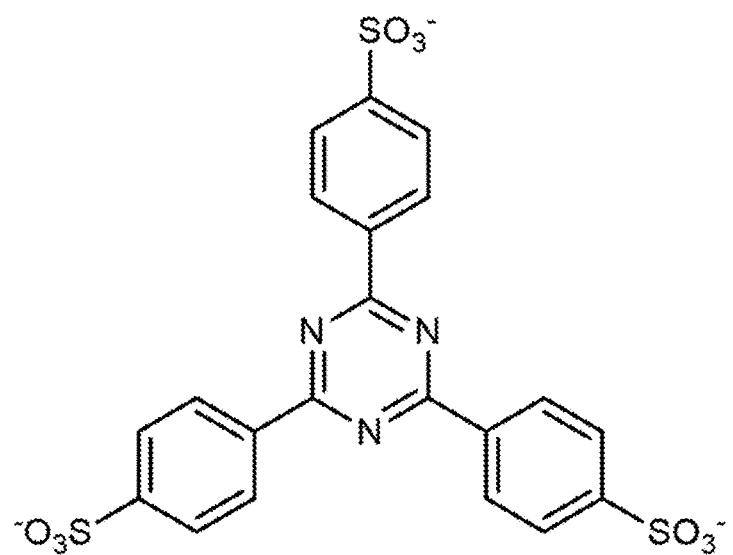

A molecular framework can comprise various organosulfonates. An organosulfonate may comprise a chiral organosulfonate. In various examples, an organosulfonate has 1, 2, 3, 4, 5, 6, or more sulfonate groups and/or one or more organic groups/moieties. Suitable examples of organosulfonates are known in the art and/or can be made by methods known in the art. Non-limiting examples of organosulfonates include those shown in FIGS. 3-5 and 8-11.

An organosulfonate can comprise various organic moieties covalently bonded to one or more sulfonate groups. An organosulfonate may comprise one or more organic moieties.

An organic group/moiety is a carbon-containing group/moiety (e.g., a hydrocarbon group/moiety). An organic group/moiety may comprise non-carbon and/or non-hydrogen atoms. Non-limiting examples of organic groups/moieties include alkyl groups/moieties, aryl groups/moieties, and substituted analogs thereof.

A molecular framework can have various architectures (topologies). Molecular framework may also be referred to as a GS framework. In various examples, a molecular framework has a lamellar (e.g., discrete bilayer lamellar and continuous lamellar), cylindrical, hexagonal, or cubic architecture (topology).

In an example, the molecular framework is not a metal-organic framework (MOF) (e.g, $[Al_8(\mu\text{-}OH)_8(HCOO)_4(1,3,$ 5-benzenetribenzoate)₄] (MOF-520) and the like) or a crystalline sponge (e.g., (ZnI₂)₃(2,4,6-tri(4-pyridyl)-1,3,5-triazine)₂ and the like). In an example, a MOF is not a MOF where the only metal is a Group I cation and/or the MOF comprises a guanidinium cation.

In various examples, the guanidinium cations and/or organosulfonate anions do not comprise an atom with atomic number (Z) equal to or greater than 8 (other than the sulfur atoms and oxygen atoms of the organosulfonate). In various examples, the molecular framework does not comprise an atom with atomic number (Z) equal to or greater than 8 (other than the sulfur atoms and oxygen atoms of the organosulfonate).

In an aspect, the present disclosure provides crystalline molecular host:small molecule guest compounds. The compounds may be referred to as inclusion compounds or inclusion complexes. The compounds comprise a molecular host (e.g., molecular framework) and one or more small molecule. The molecular host is a molecular framework disclosed herein. The small molecule guest(s) is/are encapsulated by the molecular host. In various examples, a compound is formed by a method of the present disclosure (e.g., a single-step crystallization from a suitable solvent).

A crystalline molecular host:small molecule guest compound may be in the form of a single crystal. Single crystals of a crystalline compound may have various sizes. Where the crystal is used in a structure determination method, e.g., a structure determination method of the present disclosure, it may be desirable that the crystal have a particular size (e.g., one or more dimensions, such as, for example, an edge dimension). For example, crystal size may be important with respect to the capabilities of an X-ray structure determination system (e.g., a crystal may have one or more dimension (e.g., 3 dimensions) as small as 1 micron for synchrotron X-ray source (e.g., at least 5 microns on each side crystal size is desirable) or 20 microns (e.g., at least 20 microns on each side crystal size is desirable) for a standard X-ray source, but, generally, larger crystals are desirable.

A compound can comprise various molecular hosts. A molecular host may be chiral. In an example, the molecular host and small molecule(s) are both chiral.

A desirable advantage of the GS frameworks stems from their versatility with respect to the size, shape, and physicochemical character of the inclusion cavities, which is adjustable through judicious selection of organosulfonate, and the intrinsic ability of the framework to accommodate to the size and shape of target guest molecules through hydrogen bond flexing, puckering of the GS network, and access to numerous framework isomers. Other desirable advantages include, but are not limited to: (i) syntheses of organosulfonates are generally straightforward, enabling facile expansion of the organosulfonate library; (ii) the GS inclusion compounds typically are stoichiometric owing to their synthesis by single-step crystallization, typically resulting in 100% occupancy, which can simplify structure determination of the target molecule; (iii) the aperture dimensions of crystalline sponges (5 Å×8 Å in the aforementioned sponge) places an upper limit on the size of molecules that can be accommodated. The upper limit for GDS frameworks, for example, is limited only by the height of longest organosulfonate pillar and the framework architecture (e.g., voids as wide as 15 Å can be realized in the double-brick framework isomer); (iv) the GS frameworks can include a wide range of guests, from, for example, non-polar to polar, from aliphatic to aromatic. The frameworks tolerate functional groups, except for the strongest hydrogen bond donors and acceptors; (v) the GS inclusion compounds are monomorphic, reflecting an inherent tendency to form thermodynamically preferred structures. This may be attributed to the compliance of the GS sheet and the ability to adopt different framework isomers through guest templating, both features allowing for optimum confinement of the guest molecules; (vi) guest molecules in the GS framework typically are ordered because of the custom fit provided by the "shrink wrapping" of the framework. This facilitates structure solution as well as assignment of relative stereochemistry and/or absolute configuration around stereogenic centers. In cases where disorder is observed for a particular framework, substituents can be added to the organosulfonate to enforce order through electronic or steric influence; (vii) single crystal X-ray diffraction data sets using our in-house conventional diffractometer can be collected on crystals as small as 100 μm on a side, equivalent to a volume of $10^{-6}$ cm³, which translates to less than 1 μg of target compound. This is competitive with crystalline sponges, although it is expected many targets will be available on the milligram scale; (viii) encapsulation of target molecules in the GS frameworks can be achieved through a wide range of intermolecular forces, but it is considered that covalent bond formation or specific interactions such as hydrogen bonding, charge-transfer, π-π or C—H . . . π are not required. A GS framework (e.g., a GS framework of a crystalline molecular host:small molecule guest compound) may exhibit one or more or all of these advantages.

A crystalline molecular host:small molecule guest compound can comprise various small molecules (which are also referred to herein as target compounds or guest compounds). A compound may comprise two or more small molecules (not including any solvent molecules), where each of the small molecules is structurally distinct. The small molecule(s) is/are encapsulated by the molecular host. In various examples, the small molecule(s) is/are not bonded (e.g., covalently and/or hydrogen bonded to the molecular host).

A small molecule may be neutral, uncharged, or charged. A charged small molecule may be singly or multiply positively charged and/or singly or multiply negatively charged.

In various examples, a small molecule guest is a hydrocarbon, which may comprise one or more aliphatic groups and/or moieties and/or one or more aryl groups and/or moieties. A hydrocarbon small molecule may further comprise one or more non-carbon atom (e.g., heteroatoms). Non-limiting examples of heteroatoms include (e.g., nitrogen atoms, sulfur atoms, phosphorus atoms, oxygen atoms, halogen atoms, and the like, and combinations thereof). In another example, a small molecule further comprises more metal atom (e.g., one or more neutral metal atom, one or more metal ion, and combinations thereof).

A crystalline molecular host:small molecule guest compound may comprise one or more chiral small molecules (e.g., a chiral small molecule comprising one or more chiral (stereogenic) centers). A chiral small molecule may be referred to as a stereoisomer or as a compound having one or more stereogenic center or stereocenter. The term "chiral" is used interchangeably herein with "stereogenic" and "stereo." In an example, a compound comprises a single enantiomeric form of a chiral small molecule. In another example, a compound comprises a racemic mixture of two enantiomers of a small molecule. In another example, a compound comprises one or more diastereomers of a small molecule.

It may be desirable that compound (e.g., the molecular framework and/or the small molecule) does not comprise a metal (e.g., a metal atom or metal ion).

A small molecule may be a particular stereoisomer. A small molecule can have any number (n) stereocenters (i.e., chiral tetrahedral carbon centers), but the number of stereoisomers cannot be greater than $2^n$. Non-limiting examples of chiral centers include carbon chiral centers, nitrogen chiral centers, phosphorous chiral centers, silicon chiral centers, and the like, and combinations thereof. In various examples, a small molecule guest has one or more stereocenters (e.g., 1, 2, 3, 4, 5, 6, 7, 8, 9, 10, 11, 12, 13, 14, 15 or more stereocenters). In various examples, at least one of the small molecule guests or all of the small molecule guests has one or more stereocenters (e.g., 1, 2, 3, 4, 5, 6, 7, 8, 9, 10, 11, 12, 13, 14, 15 or more stereocenters).

Small molecules can have various molecular weights. In various examples, a small molecule has a molecular weight of 100 g/mol or greater, 150 g/mol or greater, 200 g/mol or greater, 250 g/mol or greater, 300 g/mol or greater, 400 g/mol or greater, or 500 g/mol or greater. In various examples, a small molecule has a molecular weight of 100 g/mol to 1,000 g/mol, including all 0.01 g/mol values and ranges therebetween. In various examples, a small molecule has a molecular weight of 100 g/mol to 500 g/mol. The structure (e.g., relative stereochemistry and/or absolute stereochemistry) of the small molecule(s) may not be determinable by other means (e.g., means not comprising the use of a molecular host of the present disclosure) than a method of the present disclosure.

Small molecules can come from various sources. Non-limiting examples of small molecules include active pharmaceutical agents, intermediates of a process to make an active pharmaceutical agent, agrochemicals, specialty compounds, and the like.

A small molecule may have properties that make X-ray crystallographic structure determination by conventional or previous methods difficult or impossible. In various examples, a small molecule has one or more of the following properties:
 the inability to grow sufficiently large single crystals for conventional X-ray diffraction analysis;
 The small molecule alone (i.e., by itself) may not be amenable to crystallization (e.g., is a liquid or an oil under ambient conditions, for example, room temperature (e.g., 18-25° C.) and atmospheric pressure (e.g., about 1 atmosphere) and/or forms crystals that do not diffract X-rays sufficiently well for precise structure determination;
 the tendency to form oils or amorphous phases rather than crystals;
 low melting point that precludes solidification at convenient temperatures (e.g., temperatures of 0 to 50° C., including all 0.1° C. values and ranges therebetween); or
 reactivity or decomposition under ambient conditions.

Crystalline molecular host:small molecule guest compounds can have various architectures (topologies). In various examples, a molecular framework has a lamellar (e.g., discrete bilayer lamellar and continuous lamellar), cylindrical, hexagonal, or cubic architecture (topology).

Crystalline molecular host:small molecule guest compounds may have various crystalline forms. In an example, a crystalline molecular host:small molecule guest compound is a single crystal. In another example, a crystalline molecular host:small molecule guest compound comprises one or more crystalline domain having at least one dimension of 100 nm to 200 microns.

Crystalline molecular host:small molecule guest compounds can have various molecular host:small molecule ratios. In an example, a unit cell of the crystalline molecular host:small molecule compound has a 1:1 molecular host to small molecule ratio.

A compound may have more than one structurally distinct small molecule compound (not including solvent(s)) in a unit cell (e.g., a unit cell of the crystalline molecular host:small molecule compound has a 1:2, 1:3, etc. molecular host to small molecule ratio).

In an example, the molecular host has the following structure: $(C(NH_2)_3^+)_x(R\text{---}(SO_3^-)_z)_y$, and the host:guest ratio is defined as y:guest, where the ratio ranges from 1:4 to 4:1, including all ranges therebetween. In various examples, the ratio is 1:4, 1:3, 1:2, 1:1, 2:1, 3:1, or 4:1.

In an aspect, the present disclosure provides methods of making a crystalline molecular host:small molecule compound. A method can be used to make a crystalline molecular host:small molecule compound of the present disclosure. In various examples, a method is a single-step crystallization.

Notably, the GS frameworks do not crystallize alone, nor are the guest-free inclusion cavities permanent. Instead, the inclusion compounds crystallize upon adding a guest to a solution containing the GS framework components. Without intending to be bound by any particular theory, it is considered that the guest effectively serves as a template for framework assembly, driving the formation of a framework architecture that accommodates the guest in inclusion cavities. This process can be highly selective for molecular isomers (e.g., as evident from the preferential inclusion of 2,6-dimethylnaphthalene from a mixture containing all ten dimethylnaphthalene isomers in the guanidinium biphenylsulfonate framework (95% after two consecutive crystallizations)).

In various examples, a method of making a crystalline molecular host:small molecule compound comprising a molecular host and small molecule, where the small molecule is encapsulated by the molecular host, comprises: contacting (e.g., in a single step and/or a single reaction mixture) the precursors of a molecular host of the present disclosure with one or more small molecule (e.g., in a solvent), which may be a combination of structurally distinct small molecules, where a crystalline molecular host:small molecule compound is formed.

A method may be carried out in various solvents. Mixtures of solvents may be used. It is desirable that the molecular host and small molecule are at least partially soluble in the solvent. A mixture of solvents (e.g., one or more solvent containing the host framework (e.g., host framework precursors) and one or more solvent containing the target small molecule(s) that form a stable interface (e.g., immiscible solvents) may be used. It this case, formation (e.g., crystallization) of the a crystalline molecular host:small molecule compound is carried out at the interface.

The precursors of a molecular host of the present disclosure are guanidinium cations and organosulfonate anions. Non-limiting examples of organosulfonate anions are described herein. The organosulfonates may be referred to as pillars in the context of the molecular host. The guanidinium cations and an organosulfonate anions can have various counter ions. Non-limiting examples of suitable guanidinium cation counter anions are described herein and include, but are not limited to, carbonate, chloride, bromide, iodide, sulfate, and the like. Non-limiting examples of suitable organosulfonate anion counter cations include Group I cations (e.g., sodium, lithium, potassium, rubidium, and the like), ammonium, $H^+$ (e.g., where at least one of the organosulfonates is a sulfonic acid), and the like.

Mixtures of organosulfonate anions may be used. In various examples, crystallization is carried out in the presence of two, or more than one, organosulfonate anions (e.g., in a combinatorial experiment). Without intending to be bound by any particular theory, it is considered that, when two or more than one organosulfonate anions are used, only one compound with one of the molecular hosts crystallizes because that host is the most favorable (e.g., the most thermodynamically favorable host for a particular guest of the frameworks present).

In the methods, the molecular host is not preformed. For example, the molecular host (e.g., crystalline molecular host) is not formed prior to contact with the small molecule. In another example, the crystalline molecular host:small molecule compound is not formed by diffusion of the small molecule into a preformed molecular host.

Formation of a crystalline molecular host:small molecule compound (e.g., single step crystallization) can comprise various processes, which may be conventional processes. Non-limiting examples of crystallization processes include (1) slow evaporation of a solution containing the host and guest, (2) introduction of an anti-solvent, (3) layering a solution containing the guest on a solution containing the host constituents, or vice-versa, prompting crystallization at the interface between the two solutions, (4) crystallization in solution droplets in a hanging drop configuration, (5) crystallization in droplets surrounded by an immiscible non-solvent in a microfluidic crystallization device, (6) growth in a capillary for direct X-ray structure determination, and the like.

The contacting (e.g., formation of a single crystal) can be carried out in various containers. For example, one or more single crystals can be grown in a microwave conical vial, and the crystal(s) retrieved from the crystallization medium (e.g., reaction mixture comprising one or more of the following precursor(s), small molecule, solvent, and crystalline molecular host:small molecule compound by, for example, filtration or simple manual selection from the medium).

In an aspect, the present disclosure provides uses of crystalline molecular host:small molecule compounds. For example, a method of structure determination uses a crystalline molecular host:small molecule compound of the present disclosure.

Crystalline molecular host:small molecule compounds can be used in various structure determination methods. The methods can provide the structure of the molecular host and/or the small molecule. In certain examples, the methods provide the relative stereochemistry and/or absolute configuration of the molecular host and/or the small molecule.

In an example, a method of determining the structure of a small molecule comprises: subjecting a crystalline molecular host:small molecule compound of the present disclosure (e.g., a crystalline molecular host:small molecule compound of the present disclosure or made by a method of the present disclosure) to structure determination (e.g., by X-ray analysis, such as for example, X-ray crystallography), where the structure of the small molecule(s) and, optionally, the crystalline molecular host and/or the crystalline molecular host:small molecule compound is determined. The structure determination may comprise: contacting the crystalline molecular host:small molecule compound with incident electromagnetic radiation (e.g., electromagnetic radiation having a wavelength of 0.01 to 0.20 nm, including all 0.01 nm values and ranges therebetween) (e.g., X-ray radiation, which may be in the form of an X-ray beam); collecting diffraction image data created by diffraction (e.g., elastic diffraction) of the incident electromagnetic radiation by the crystalline molecular host:small molecule compound (e.g., measuring, for the example, the intensity and diffraction angle, of at least a portion of the diffracted electromagnetic radiation or one or more diffracted wavelengths of the incident electromagnetic radiation); and determining the structure of the small molecule and, optionally, the crystalline molecular host and/or the crystalline molecular host:small molecule compound.

One or more or all of the small molecules may have one or more stereogenic centers. In an example, at least one or all of the small molecules has one or more stereogenic centers and the relative stereochemistry and/or the absolute configuration of one or more of the stereogenic centers in the small molecule(s) is/are determined.

In various examples, a method of structure determination uses X-ray crystallographic methods to determine the structure of the molecular host and/or the small molecule. Various X-ray crystallographic methods can be used. Numerous suitable X-ray crystallographic methods, X-ray crystallography systems and instruments, etc. are known in the art.

X-rays for structure determination can be provided by various sources. Numerous suitable sources are known in the art. In various examples, the electromagnetic radiation (e.g., the incident electromagnetic radiation) is provided by a synchrotron, rotating anode, microfocus source, or the like. For example, a source is a conventional X-ray tube, e.g., Mo (0.71 Å or 0.071 nm emission wavelength) and Cu (1.54 Å or 0.154 nm emission wavelength). In another example, the source is a synchrotron source. The emission of a synchrotron is tunable (the emission wavelength may be selected).

Using the diffraction data created by diffraction (e.g., elastic diffraction) of the incident electromagnetic radiation by the crystalline molecular host:small molecule compound (e.g., measuring, for example, the intensity and diffraction angle, of at least a portion of the diffracted electromagnetic radiation or one or more diffracted wavelengths of the incident electromagnetic radiation) the structure of the small molecule and, optionally, the crystalline molecular host and/or the crystalline molecular host:small molecule compound can be determined by various methods. Numerous suitable methods are known in the art. In various examples, the determining is carried out using a heavy-atom method.

The crystalline molecular host:small molecule compound may be a single crystal. For example, where the molecular structure and/or absolution configuration is determined, the important, the crystalline molecular host:small molecule compound is a single crystal.

The structure of the small molecule(s) and/or the crystalline molecular host and/or the crystalline molecular host:small molecule compound may be determined without the use of one or more structure determination aids. Non-limiting examples of structure determination aids include heavy atoms, chiral auxiliaries, and the like. In various examples, the compound does not comprise a structure determination aid (e.g., other than the sulfur atom(s) of the organosulfonate of the molecular host).

The structure of the small molecule(s) and/or the crystalline molecular host and/or the crystalline molecular host:small molecule compound may be determined without the use of one or more heavy atoms. For example, where a small molecule or small molecules and/or crystalline molecular host does not comprise an atom with atomic number (Z) equal to or greater than 8 (other than the sulfur atoms and oxygen atoms of the organosulfonate), the crystalline molecular host:small molecule compound is determined by a method of the present disclosure.

In the case where the small molecule(s) and/or the crystalline molecular host or the crystalline molecular host:small molecule compound is chiral, the relative stereochemistry and/or absolute configuration of one or more or all of the stereogenic centers in the small molecule(s) and/or the crystalline molecular host or the crystalline molecular host:small molecule compound, and the stereochemistry of the small molecule(s) and/or the crystalline molecular host or the crystalline molecular host:small molecule compound may be determined. In various examples, the small molecule(s) and/or the crystalline molecular host or the crystalline molecular host:small molecule compound is/are enantiomer(s)/enantiomeric, diastereomer(s)/diastereomeric, or a combination thereof.

In the case where the small molecule(s) and/or the crystalline molecular host or the crystalline molecular host:small molecule compound is chiral, the structure of the small molecule(s) and/or the crystalline molecular host or the crystalline molecular host:small molecule compound can be determined without the use of auxiliary components. Such auxiliary components are known in the art. In an example, the structure of a chiral small molecule and/or a chiral crystalline molecular host or a chiral crystalline molecular host:small molecule compound is determined without the use of auxiliary component (e.g., a chiral cationic auxiliary, and the like).

The structure determination can provide structure determination with desirable quality (precision). $R_1$, which may be referred to as residual factor or reliability factor, is considered a measure of the quality (precision) of a structure determination. In various examples, where the small molecule(s) and/or the crystalline molecular host or the crystalline molecular host:small molecule compound is/are achiral and/or chiral, the structure of the small molecule and, optionally, the crystalline molecular host and/or the crystalline molecular host:small molecule compound is determined with an $R_1$ value 0.2 or less, 0.15 or less, 0.1 or less, or 0.05 or less. In various examples, the structure of the small molecule and, optionally, the crystalline molecular host and/or the crystalline molecular host:small molecule compound is determined with an $R_1$ value of 0.01 to 0.2, including all 0.01 values and ranges therebetween.

The Flack parameter is a measure of the quality of the structure determination of chiral systems. Mathematically, the Flack parameter should be in the range of 0-1, but in practice it can be slightly less than 0 or slightly greater than 1. The precision of the structure determination relies on the standard uncertainty, which significantly depends on the intensity and data redundancy. Typically, 0.01(3) or −0.01(3) is considered to be a reliable value for assigning the correct absolute configuration of a stereogenic center. In various examples, where the small molecule(s) and/or the crystalline molecular host or the crystalline molecular host:small molecule compound is a chiral (e.g., a single enantiomer), the Flack parameter or the absolute value of the Flack parameter is 0 to 0.1, 0 to 0.05, or 0 to 0.01. In various other examples, the Flack parameter or the absolute value of the Flack parameter is 0 to 0.1, 0 to 0.05, or 0 to 0.01 and/or 0.2 or less, 0.15 or less, 0.1 or less, or 0.05 or less (e.g., 0.01 to 0.2). In various examples, a method is carried out with a precision (e.g., a $R_1$ value) and a Flack parameter as described herein.

The compound may have one or more solvent molecules present in the crystalline structure. Typically, the solvent is ordered and does not affect structure refinement. It the solvent is disordered, typically the disorder can be modeled because the solvent is typically stoichiometric or at least present in a well-defined amount (which is in contrast to crystalline sponges where solvent is often included in ill-defined and substantial amounts). In various examples, the crystalline molecular host:small molecule guest compound does not comprise a detectable (e.g., by X-ray crystallographic methods, such as, for example, X-ray crystallographic methods of the present disclosure) solvent molecule.

The compound may exhibit disorder. In an example, the crystalline molecular host does not exhibit detectable (e.g., by X-ray crystallographic methods, such as, for example, X-ray crystallographic methods of the present disclosure) disorder.

The steps of the method described in the various embodiments and examples disclosed herein are sufficient to carry out the methods of the present disclosure. Thus, in an embodiment, a method consists essentially of a combination of the steps of the methods disclosed herein. In another embodiment, a method consists of such steps.

The following examples are presented to illustrate the present disclosure. They are not intended to be limiting in any matter.

Example 1A

This example provides an example of a crystalline molecular framework:small molecule compound of the present disclosure and a method of making the compound and a method of structure determination of the present disclosure.

Evaporation of a methanol solution containing guanidinium 2,6-anthracenedisulfonate (GADS) and guaiazulene afforded blue single crystals with the formula $(G_2ADS)$. (guaiazulene)$_2$ (1A). Single crystal X-ray diffraction determined that the compound crystallized in the Pbca space group (a=13.15 Å, b=12.78 Å, c=26.57 Å, V=4463 Å$^3$) with the zigzag brick architecture. The guaiazulene target was slightly disordered, with two components in a ratio of 94:6. The molecular structure of the major disordered component was refined freely without any restraints and constraints.

Example 1B

This example provides an example of a crystalline molecular framework:small molecule compound of the present disclosure and a method of making the compound and a method of structure determination of the present disclosure.

Evaporation of a methanol solution containing guanidinium 4,4'-biphenyldisulfonate ($G_2BPDS$) and guaiazulene afforded blue single crystals with the formula ($G_2NDS$). (guaiazulene)$_2$ (1B). Single crystal X-ray diffraction determined that the compound crystallized in the Pbca space group (a=13.89 Å, b=12.98 Å, c=24.76 Å, V=4462 Å$^3$) with the zigzag brick architecture. The guaiazulene target was slightly disordered, with four components in a ratio of 44:25:21:10. The molecular structure of the major disordered component was refined freely without any restraints and constraints.

Example 2

This example provides an example of a crystalline molecular framework:small molecule compound of the present disclosure and a method of making the compound and a method of structure determination of the present disclosure.

Evaporation of a methanol solution containing guanidinium 2,5-naphthalenedisulfonate ($G_2NDS$) and azulene afforded blue single crystals with the formula ($G_2NDS$). (azulene)$_3$. (2). Single crystal X-ray diffraction determined that the compound crystallized in the P2$_1$/n space group ($a=7.61$ Å, $b=21.40$ Å, $c=11.93$ Å, $\beta=90.75°$, $V=1942$ Å$^3$) with the simple brick architecture. Despite slight disorder, the molecular structure of the azulene target was refined satisfactorily and the structure found identical to its previously reported structure.

Example 3

This example provides an example of a crystalline molecular framework:small molecule compound of the present disclosure and a method of making the compound and a method of structure determination of the present disclosure.

Evaporation of a methanol solution containing guanidinium 4,4'-biphenyldisulfonate (G$_2$BPDS) and 2,6-diisopropylaniline afforded block shaped single crystals of (G$_2$BPDS).(2,6-diisopropylaniline)$_2$ (3). Single-crystal X-ray diffraction determined that the compound crystallized in the P212121 space group ($a=12.58$ Å, $b=13.96$ Å, $c=24.54$ Å, $V=4312$ Å$^3$) with the simple brick architecture. The structure was refined successfully with no constraints, consistent with dense packing of guest molecules in the framework.

Example 4

This example provides an example of a crystalline molecular framework:small molecule compound of the present disclosure and a method of making the compound and a method of structure determination of the present disclosure.

Evaporation of a methanol solution containing guanidinium [1,1'-biphenyl]-1-sulfonate (GBPMS) and (S)-(+)-carvone, a low melting point (25.2° C.) compound containing one chiral center, afforded single crystals of (GBPMS).((S)-(+)-carvone) (4). Single-crystal X-ray diffraction determined that the compound crystallized in the P212121 space group ($a=7.51$ Å, $b=12.06$ Å, $c=25.59$ Å, $V=2316$ Å$^3$). The guest molecules were refined with no restraint or constraint. The Flack parameter, which reflects the correctness of chirality assignment, was found to be 0.02(3), indicating definitive determination of absolute configuration.

Example 5

This example provides an example of a crystalline molecular framework:small molecule compound of the present disclosure and a method of making the compound and a method of structure determination of the present disclosure.

Evaporation of a methanol solution containing guanidinium 2,5-naphthalenedisulfonate (G$_2$NDS) and (3aR)-(+)-Sclareolide, a sesquiterpene lactone with four chiral centers that is often used as a fragrance in the cosmetics industry, afforded single crystals of (G$_2$NDS).((3 aR)-(+)-Sclareolide) (5). Single-crystal X-ray diffraction determined that the compound crystallized in the space group P2$_1$2$_1$2$_1$ ($a=12.87$ Å, $b=14.54$ Å, $c=18.54$ Å, $V=3469$ Å$^3$), with the (3aR)-(+)-Sclareolide guest aligned along the inclusion channels in the so-called "V-brick" architecture. The Flack parameter, which reflects the correctness of chirality assignment, was found to be 0.07(4), indicating definitive determination of absolute configuration.

Example 6

This example provides an example of a crystalline molecular framework:small molecule compound of the present disclosure and a method of making the compound and a method of structure determination of the present disclosure.

Evaporation of a methanol solution containing guanidinium 2,5-naphthalenedisulfonate (G$_2$NDS) and drospirenone, a progestin used in birth control drugs, afforded single crystals (G$_2$NDS).(drospirenone).(methanol) (6). Single-crystal X-ray diffraction determined that the compound crystallized in the P1 space group ($a=12.13$ Å, $b=12.49$ Å, $c=14.16$ Å, $\alpha=92.66°$, $\beta=91.26°$, $\gamma=116.19°$, $V=1934$ Å$^3$) with the so-called "zigzag brick" architecture. The Flack parameter, which reflects the correctness of chirality assignment, was found to be 0.03(5), indicating definitive determination of absolute configuration. The previously reported absolute structure of drospirenone could only be determined through synthetic procedures due to lack of heavy atoms.

Example 7

This example provides an example of a crystalline molecular framework:small molecule compound of the present disclosure and a method of making the compound and a method of structure determination of the present disclosure.

Evaporation of a methanol solution containing guanidinium 4,4'-biphenyldisulfonate (G$_2$BPDS) and progesterone, a female sex hormone, afforded single crystals (G$_2$BPDS).(Progesterone).(ethanol) (7). Single-crystal X-ray diffraction determined that the compound crystallized in the P2$_1$2$_1$2$_1$ space group ($a=11.28$ Å, $b=26.27$ Å, $c=27.80$ Å, $V=8235$ Å$^3$) with the "simple brick" architecture wherein two progesterone molecules lay back to back perpendicular to the BPDS pillars. The Flack parameter, which reflects the correctness of chirality assignment, was found to be 0.10(4). While this value is slightly larger than the other examples in this application, this can be attributed to the small size of the crystal examined and the associated low intensity of diffraction from the sample. Nonetheless, the measured Flack parameter is within the range required for confident assignment of the absolution configuration.

Example 8

This example provides an example of a crystalline molecular framework:small molecule compound of the present disclosure and a method of making the compound and a method of structure determination of the present disclosure.

Evaporation of a methanol solution containing guanidinium 4,4'-stilbenedisulfonate (G$_2$SDS) and 7-acetyl-5,8-dihydroxy-4-isopropyl-1-methylbicyclo[4.3.0]nonane, a hydrophilic carotol derivative that contains two hydroxyl groups, afforded single crystals of (G$_2$SDS)).(7-acetyl-5,8-dihydroxy-4-isopropyl-1-methylbicyclo[4.3.0]nonane)$_{0.5}$ (8). Single-crystal X-ray diffraction determined that the compound crystallized in the P1 space group ($a=7.61$ Å, $b=12.02$ Å, $c=32.01$ Å, $\alpha=87.01°$, $\beta=86.31°$, $\gamma=89.99°$, $V=2918$ Å$^3$) with the so-called "crisscross" architecture, in which two adjacent disulfonate pillars form the shape of a cross leaving a cavity that accommodates the target guest molecule.

Example 9

This example provides an example of a crystalline molecular framework:small molecule compound of the present disclosure and a method of making the compound and a method of structure determination of the present disclosure.

Evaporation of a methanol solution containing guanidinium tri(4-sulfophenyl)benzene ($G_3$TSPHB), isophorone and neryl acetate afforded single crystals of ($G_3$TSPHB).(neryl acetate).(isophorone)$_3$ (9). Single-crystal X-ray diffraction determined that the compound crystallized in $P2_12_12_1$ space group (a=7.57 Å, b=24.67 Å, c=39.62 Å, V=7402 Å$^3$), in which the guests are tightly confined in three crystallographically distinct channels, Pairs of isophorone molecules fill in two of the channels that are flanked by two adjacent trisulfonate molecules, and one additional equivalent of isophorone is found in the third channel. The isophorone molecules anchor the neryl acetate, which is sandwiched by two TSPHB molecules through π-stacking in its position, thereby precluding disorder of the targeted guest. The inclusion of the isophorone molecules in the channels precludes inclusion of neryl acetate in these regions, such that disorder from multiple occupancy is obviated.

Example 10

This example provides an example of a crystalline molecular framework:small molecule compound of the present disclosure and a method of making the compound and a method of structure determination of the present disclosure.

Evaporation of an aqueous methanol solution at 40° C. containing guanidinium tetra(4-sulfophenyl)benzene ($G_4$TSPB) and pancuronium bromide, a dicationic aminosteroid muscle relaxant, afforded single crystals of ($G_6$(1,1'-((2S,3S,5S,8R,9S,10S,13S,14S,16S,17R)-3,17-dihydroxy-10,13-dimethylhexadecahydro-1H-cyclopenta[a]phenanthrene-2,16-diyl)bis(1-methylpiperidin-1-ium))$_2$.((TSPB)$_2$.(H$_2$O)$_4$) (which may be referred to as $G_6$.(deacetylated pancuronium)(TSPB)$_2$.(H$_2$O)$_4$). (10). Single-crystal X-ray diffraction determined that the compound crystallized in the C2 space group (a=36.03 Å, b=19.83 Å, c=18.78 Å, β=117.72°, V=11877 Å$^3$). The X-ray diffraction data indicated that the guest was deacetylated pancuro resulting from hydrolysis of the pancuronium acetyl groups during crystallization, demonstrating that reaction products could be captured in the guanidinium sulfonate framworks. Furthermore, the X-ray data confirmed that the stereochemistry about the chiral centers was unaffected by hydrolysis as well as crystallization. The Flack parameter, which reflects the correctness of chirality assignment, was found to be 0.02(2). Previously, the absolute configuration was assigned by X-ray diffraction assisted by anomalous scattering, but the coordinates were derived to conform with stereochemistry determined by other means.

Example 11

This example provides a comparison of structure determination using prior art methods for comparison with the instant methods.

Table 2. Comparison of the structure refinement for guaiazulene and 2,6-diisopropylaniline using the single-step crystallization GS framework method of the present disclosure (GS) with a crystalline sponge method (CSM) and an optimized crystalline sponge method.

| Compound | Method | $R_1$ | $wR_2$ | GoF | Number of restraints | Occupancy | Squeeze? Y/N |
|---|---|---|---|---|---|---|---|
| Guaiazulene | GS | 0.0424 | 0.1059 | 1.039 | 0 | 1 | No |
|  | CSM | 0.0859 | 0.3021 | 1.097 | 71 | ~0.6 | Yes |
|  | CSM optimized | 0.0379 | 0.1035 | 1.056 | 0 | ~1 | No |
| 2,6-diisopropylaniline | GS | 0.0302 | 0.0829 | 1.037 | 0 | 1 | No |
|  | CSM | 0.1182 | 0.3520 | 1.082 | 64 | ~0.75 | Yes |
|  | CSM optimized | 0.0653 | 0.1541 | 1.128 | 78 | ~1 | No |

Example 12

This example provides an example of a crystalline molecular framework:small molecule compound of the present disclosure and a method of making the compound and a method of structure determination of the present disclosure.

Artemisinin, a widely used antimalarial drug that was originally derived from the extract of *Artemisia annua* L., crystalized with guanidinium 4,4'-stilbenedisulfonate to afford ($G_2$SDS)⊃(artemisinin) single crystals in the space group group $P222_1$. Artemisinin molecules were confined in channels of crisscross bilayer architecture wherein the sulfonate nodes of 4,4'-stilbenedisulfonate pillars alternate on adjacent major ribbons along each channel. Though disorder occurred, the two components of guest molecules and the two components of the organic pillar could be modeled and refined unambiguously. The Flack parameter was refined as −0.03(10), indicating convincing absolute configuration assignment.

Example 13

This example provides an example of a crystalline molecular framework:small molecule compound of the present disclosure and a method of making the compound and a method of structure determination of the present disclosure.

A highly polymorphic organic compound 5-methyl-2-[(2-nitrophenyl)amino]-3-thiophenecarbonitrile (also known as ROY because of its red, orange and yellow colors in its 11 polymorphs) was dissolved in a 2:1 v/v mixture of methanol:acetonitrile solution containing guanidinium 4,4'-diphenyletherdisulfonate ($G_2$DPEDS), guanidinium 4,4'-biphenyldisulfonate ($G_2$BPDS) and guanidinium 2,6-anthracenedisulfonate (GADS). Each guanidinium salt was added in equimolar to ROY. After 24 hours of solvent evaporation, yellow single crystals of $G_2$ADS⊃(ROY)$_2$ formed on the wall and bottom of the 5 mL borosilicate glass test tube concomitantly with colorless crystalline whiskers of other guest-free GS apohosts and small amount of free ROY crystals.

A separate experiment in similar conditions with $G_2$DPEDS and ROY did not yield $G_2$DPE⊃(ROY)$_x$ inclusion compounds, indicating $G_2$DPEDS not being a suitable host for ROY in such conditions. Another crystallization experiment with G$_2$BPDS and ROY yielded a small amount of G$_2$BPDS⊃ROY embedded in concomitantly formed guest free ROY crystals and guest-free GS apohost, indicating that G$_2$BPDS forms inclusion compound with ROY. Different from the crystallization of G$_2$ADS⊃(ROY)$_2$, G$_2$BPDS⊃ROY crystals typically form at the bottom of the borosilicate glass test tube, which indicates a slower crystallization process of G$_2$BPDS⊃ROY, possibly caused by its higher solubility. Interestingly, G$_2$BPDS⊃ROY has more disorder compared to G$_2$ADS⊃(ROY)$_2$, the inclusion compound formed in the mixture of apohosts.

The formation of G$_2$ADS⊃(ROY)$_2$ from a mixture of ROY, G$_2$DPEDS, G$_2$BPDS and G$_2$ADS indicates that a best fit host for a certain target molecule will be automatically "selected" by the guest molecule in a mixture of hosts. This would reduce the number of trial-errors by mixing several pre-selected GS hosts in one solution with certain target molecules, especially when small amount (typically less than 1 mg) of sample is available.

Although the present disclosure has been described with respect to one or more particular embodiments and/or examples, it will be understood that other embodiments and/or examples of the present disclosure may be made without departing from the scope of the present disclosure.

The invention claimed is:

1. A method of determining the structure of a small molecule comprising:
    subjecting a crystalline molecular framework:small molecule compound to structure determination by X-ray analysis, wherein the structure of one or more or all of the small molecule(s) and, optionally, the molecular framework and/or the crystalline molecular:small molecule compound is determined,
    wherein the crystalline molecular framework:small molecule compound comprises a molecular framework and one or more small molecules,
    the molecular framework comprises a plurality of guanidinium cations and a plurality of organosulfonate anions,
    the guanidinium cations and organosulfonate anions are associated via one or more hydrogen bond and the small molecule(s) is/are encapsulated by the molecular framework, and
    at least one small molecule or all of the small molecules has/have one or more stereocenters and the relative stereochemistry and the absolute configuration of one or more of the stereogenic centers in the small molecule(s) is/are determined.

2. The method of claim 1, wherein the structure determination comprises:
    contacting the crystalline molecular framework:small molecule compound with incident X-ray radiation;
    collecting diffraction image data created by diffraction of the incident X-ray radiation by the crystalline molecular framework:small molecule compound; and
    determining the structure of one or more or all of the small molecule(s) and, optionally, the molecular framework and/or the crystalline molecular framework:small molecule compound.

3. The method of claim 2, wherein the incident X-ray radiation is provided by a synchrotron, rotating anode, or microfocus source.

4. The method of claim 1, wherein the determining is carried out using a heavy-atom method.

5. The method of claim 1, wherein one or more or all of the structures of the small molecule(s) and, optionally, the molecular framework and/or the crystalline molecular framework:small molecule compound, is determined with an $R_1$ value 0.2 or less.

6. The method of claim 1, wherein the plurality of organosulfonate anions is chosen from organomonosulfonate anions and organopolysulfonate anions.

7. The method of claim 6, wherein the organopolysulfonates anions are chosen from organodisulfonates anions, organotrisulfonates anions, organotetrasulfonates anions, and organopentasulfonate anions.

8. The method of claim 1, wherein the compound is a single crystal.

9. The method of claim 1, wherein the compound comprises one or more crystalline domain having at least one dimension of 100 nm to 200 μm.

10. The method of claim 1, wherein each small molecule is a hydrocarbon.

11. The method of claim 1, wherein the molecular framework does not comprise a metal and/or the small molecule does not comprise a metal atom or metal ion.

12. The method of claim 1, wherein the one or more stereocenters is chosen from carbon stereocenters, nitrogen stereocenters, phosphorous stereocenters, silicon stereocenters, and combinations thereof.

13. The method of claim 1, wherein each small molecule has a molecular weight of 100 g/mol or greater.

14. The method of claim 1, wherein each small molecule is an active pharmaceutical agent, agrochemical, specialty compound, or an intermediate of a process to make an active pharmaceutical agent, agrochemical, or specialty compound.

15. The method of claim 1, wherein the compound does not comprise a structure determination aid.

16. The method of claim 1, further comprising making the crystalline molecular framework:small molecule compound, the making comprising contacting one or more guanidinium cation precursor and one or more organosulfonate anion precursor with one or more small molecule, wherein the crystalline molecular framework:small molecule compound is formed.

17. The method of claim 16, wherein the contacting is carried out in a single step and/or a single reaction mixture.

18. The method of claim 1, wherein one or more or all of the structures of the small molecule(s) and, optionally, the molecular framework and/or the crystalline molecular framework:small molecule compound, is determined with an $R_1$ value 0.2 or less and an absolute value of the Flack parameter of 0.2 or less.

* * * * *